United States Patent
Whitlock et al.

(10) Patent No.: US 9,533,989 B2
(45) Date of Patent: Jan. 3, 2017

(54) SUBSTITUTED PYRIMIDINE-5-CARBOXAMIDES AS SPLEEN TYROSINE KINASE INHIBITORS

(71) Applicant: Ziarco Pharma Ltd, Canterbury, Kent (GB)

(72) Inventors: Gavin A. Whitlock, Sandwich (GB); Paul Alan Glossop, Sandwich (GB)

(73) Assignee: Ziarco Pharma Ltd., Sandwich (GB)

( * ) Notice: Subject to any disclaimer, the term of this patent is extended or adjusted under 35 U.S.C. 154(b) by 0 days.

(21) Appl. No.: 14/428,808

(22) PCT Filed: Sep. 18, 2013

(86) PCT No.: PCT/GB2013/052440
§ 371 (c)(1),
(2) Date: Mar. 17, 2015

(87) PCT Pub. No.: WO2014/045029
PCT Pub. Date: Mar. 27, 2014

(65) Prior Publication Data
US 2015/0232470 A1    Aug. 20, 2015

Related U.S. Application Data

(60) Provisional application No. 61/702,285, filed on Sep. 18, 2012.

(51) Int. Cl.
| | |
|---|---|
| *A61K 31/505* | (2006.01) |
| *C07D 239/48* | (2006.01) |
| *C07D 487/04* | (2006.01) |
| *C07D 471/04* | (2006.01) |
| *C07D 403/12* | (2006.01) |

(52) U.S. Cl.
CPC ........... *C07D 487/04* (2013.01); *C07D 239/48* (2013.01); *C07D 403/12* (2013.01); *C07D 471/04* (2013.01)

(58) Field of Classification Search
CPC ........................... A61K 31/505; C07D 239/48
USPC ... 514/275; 544/297; 546/143, 171; 548/469
See application file for complete search history.

(56) References Cited

U.S. PATENT DOCUMENTS

| 6,106,864 A | 8/2000 | Dolan et al. |
| 2010/0048567 A1 | 2/2010 | Jia et al. |

FOREIGN PATENT DOCUMENTS

| EP | 1184376 A1 | 3/2002 |
| WO | WO 91/11172 A1 | 8/1991 |
| WO | WO 94/02518 A1 | 2/1994 |
| WO | WO 98/55148 A1 | 12/1998 |
| WO | WO 00/35298 A1 | 6/2000 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Cooley LLP; Ivor R. Elrifi; Christina K. Stock

(57) ABSTRACT

The present invention relates to compounds of formula (Ia), (Ib) or (Ic):

(I)

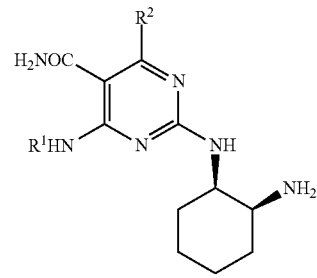

(Ia)

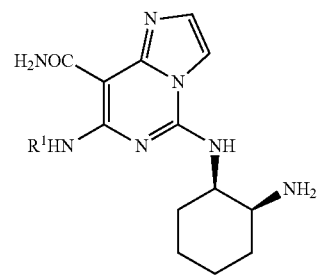

(Ib)

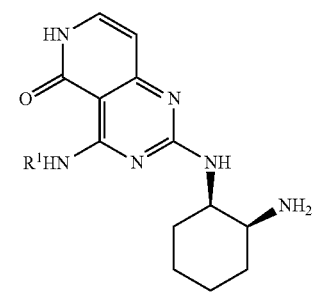

(Ic)

to pharmaceutically acceptable salts therefore and to pharmaceutically acceptable solvates of said compounds and salts, wherein the substituents are defined herein; to compositions containing such compounds; and to the uses of such compounds in the treatment of various diseases, particularly asthma, COPD, allergic rhinitis, chronic sinusitis, atopic dermatitis, psoriasis, rosacea, alopecia, allergic conjunctivitis and dry eye disease.

8 Claims, 1 Drawing Sheet

(56) References Cited

FOREIGN PATENT DOCUMENTS

| WO | 2009136995 A2 | 11/2009 |
| WO | WO 2009/136995 A2 | 11/2009 |
| WO | 2011053861 A1 | 5/2011 |

OTHER PUBLICATIONS

Vippagunta, et al. Advanced Drug Delivery Reviews, 48, 2001, 18.*
Lagerstrom et al., "Structural diversity of G protein-coupled receptors and significance for drug discovery", *Nature Reviews/Drug Discovery*, vol. 7, p. 339-358, (2008).
Smith D. "Do prodrugs deliver?", *Current Opinion in Drug Discovery and Development*, vol. 10, No. 5, p. 550-559, (2007).
Almarsson et al. "Crystal engineering of the composition of pharmaceutical phases. Do pharmaceutical co-crystals represent a new path to improved medicines?", Chem Commun, 17, p. 1889-1896, (2004).
Haleblian J. "Characterization of Habits and Crystalline Modification of Solids and Their Pharmaceutical Applications", Journal of Pharmaceutical Sciences, vol. 64, No. 8, p. 1269-1288, (Aug. 1975).
Smith "Chiral Chromatography Using Suband Supercritical Fluids", *Chromatographic Science Series*, vol. 75, pp. 223-249, (1998).
Liang et al., "Fast-dissolving intraoral drug delivery systems", Expert Opinion in Therapeutic Patents, vol. 11, No. 6, p. 981-986, (2001).
Verma et al., "Drug Delivery Technologies and Future Directions", Pharmaceutical Technology On-line, vol. 25, No. 2, p. 1-14, (2001).
International Search Report and Written Opinion, PCT Application No. PCT/GB2013/052440 dated Jan. 7, 2014, 17 pages.
Lagerstrom, M. C. et al. "Structural diversity of G protein-coupled receptors and significance for drug discovery" *Nature Reviews/Drug Discovery*, vol. 7, pp. 339-357, (2008).
Smith, D. A. "Do prodrugs deliver?" *Current Opinion in Drug Discovery and Development*, vol. 10, No. 5, pp. 550-559, (2007).
Almarsson, O. et al. "Crystal engineering of the composition of pharmaceutical phases. Do pharmaceutical co-crystals represent a new path to improved medicines?" *Chem. Commun.*, 17, pp. 1889-1896, (2004).
Haleblian, J. "Characterization of Habits and Crystalline Modification of Solids and Their Pharmaceutical Applications ", Journal of Pharmaceutical Sciences, vol. 64, No. 8, pp. 1269-1288, (1975).
Smith, R. H. "Chiral Chromatography Using Sub- and Supercritical Fluids" *Chromatographic Science Series*, vol. 75, pp. 223-249, (1998).
Liang, A. C. et al. "Fast-dissolving intraoral drug delivery systems", Expert Opinion in Therapeutic Patents, vol. 11, No. 6, pp. 981-986, (2001).
Verma, R. K. et al. "Current Status of Drug Delivery Technologies and Future Directions", Pharmaceutical Technology On-line, vol. 25, No. 2, pp. 1-14, (2001).

* cited by examiner

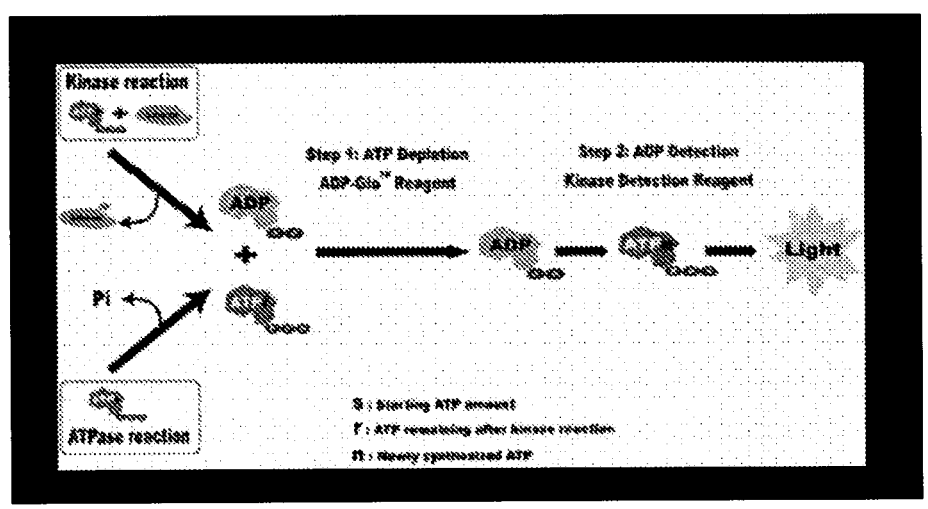

SUBSTITUTED PYRIMIDINE-5-CARBOXAMIDES AS SPLEEN TYROSINE KINASE INHIBITORS

CROSS-REFERENCE TO RELATED APPLICATIONS

This application is a U.S. National Stage Application under 35 U.S.C. §371 of International Application No. PCT/GB2013/052440, filed Sep. 18, 2013, which claims priority to U.S. Provisional Application No. 61/702,285, filed Sep. 18, 2012, Each of the above-referenced applications is expressly incorporated by reference herein its entirety.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND

Allergic inflammatory conditions are largely the manifestation of binding of allergen specific IgE to high affinity IgE receptors (FcεRI) on mast cells and basophils. FcεRI cross linking by allergen-IgE complexes results in degranulation and the subsequent release of preformed acute inflammatory mediators (e.g. histamine, tryptase), de novo synthesized arachidonic acid (AA) metabolites (e.g. leukotriene LTC4, prostaglandin D2) and a range of cytokines and chemokines. The acute mediators and AA metabolites result in the early phase allergic response (EAR), characterized by increased vascular permeability, smooth muscle contraction, and the initial influx of inflammatory cells. The late phase allergic response (LAR) is characterized by cytokine- and chemokine-mediated activation and recruitment of additional inflammatory cells (eosinophils, macrophages, T cells). Inhibition of mast cell and basophil degranulation therefore represents an effective approach to the treatment of allergic inflammatory disorders such as asthma, allergic rhinitis, food allergy, allergic conjunctivitis and allergic skin diseases.

Spleen Tyrosine Kinase (SYK) is a non-receptor protein tyrosine kinase of 72 KD, which regulates FcεRI and FcγR signaling in mast cells and basophils and is widely expressed in a variety of inflammatory cells. SYK is upstream of the signaling cascades which regulate calcium flux and gene transcription, and is therefore essential for the production and secretion of both early and late allergic inflammatory mediators in response to allergen-IgE complexes. The critical role of SYK in regulating the degranulatory response is supported by the following observations: (i) SYK−/− murine mast cells fail to produce histamine, LTC4 and TNFα when stimulated through FcεRI; (ii) 10-20% of humans have a "non releaser" basophil phenotype in which these cells fail to degranulate in response to IgE crosslinking; this is due to a cell lineage-restricted and reversible SYK deficiency and (iii) small molecule SYK inhibitors dose-dependently block acute mediator and cytokine release from human mast cells.

There is therefore a need to provide novel inhibitors of SYK which have therapeutic potential in the treatment of allergic conditions and diseases.

BRIEF SUMMARY

The present invention relates to pyrimidine derivatives, pharmaceutical compositions comprising such compounds and their use as medicaments. More particularly, the present invention provides pyrimidine derivatives which are Spleen Tyrosine Kinase (SYK) inhibitors and useful for the treatment of allergic and respiratory conditions, particularly asthma, COPD, allergic rhinitis, chronic sinusitis, atopic dermatitis, psoriasis, rosacea, alopecia, allergic conjunctivitis and dry eye disease

BRIEF DESCRIPTION OF THE SEVERAL VIEWS OF THE DRAWING(S)

FIG. 1 is a schematic of the Promega ADP-Glo Kinase Assay.

DETAILED DESCRIPTION

The invention therefore provides, as embodiment E1, a compound of formula (Ia), (Ib) or (Ic):

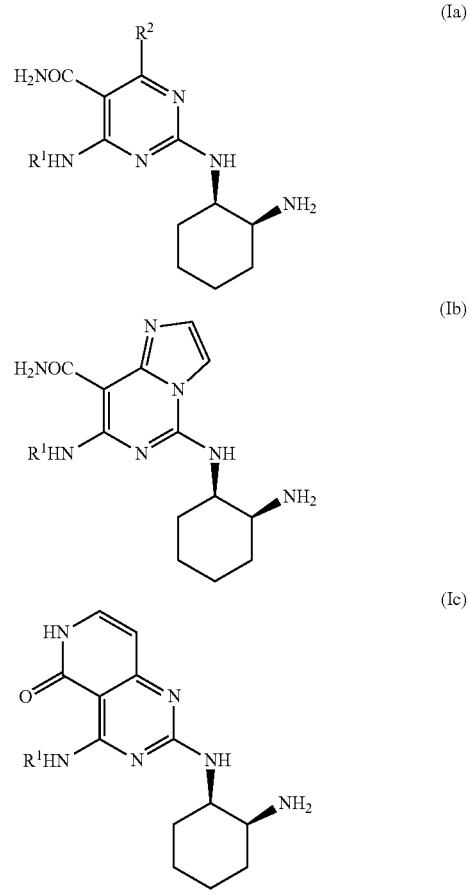

or a pharmaceutically acceptable salt thereof, or a pharmaceutically acceptable solvate of said compound or pharmaceutically acceptable salt, wherein:

$R^1$ is (i) a 9-membered bicyclic aromatic heterocycle containing either (a) 1-4 N atoms or (b) 1 O or S atom and 0-3 N atoms, said heterocycle being optionally substituted by 1 $R^3$ group and 1-3 $R^4$ groups or (ii) a biphenyl, benzylphenyl, phenoxyphenyl or phenylthiophenyl group, said group being optionally substituted by 1-3 $R^4$ groups;

$R^2$ is H or OH;

$R^3$ is —(CH$_2$)$_n$—Ar, wherein n is 0-4 and Ar is a phenyl group optionally substituted by 1-3 $R^4$ groups;

$R^4$ is selected independently in each case from $C_1$-$C_6$ alkyl, $C_3$-$C_8$ cycloalkyl, halo, —CN, —OR$^5$, —NR$^6$R$^7$, —SR$^5$, —SOR$^8$, —SO$_2$R$^8$, —COR$^5$, —OCOR$^5$, —COOR$^5$, —NR$^5$COR$^5$, —CONR$^6$R$^7$, —NR$^5$SO$_2$R$^8$, —SO$_2$NR$^6$R$^7$, —NR$^5$CONR$^6$R$^7$, —NR$^5$COOR$^8$, —NR$^5$SO$_2$NR$^6$R$^7$, —COR$^9$ and —COOR$^9$, where —COR$^9$ and —COOR$^9$, only attach via the N atom of $R^1$ $R^5$ is H, $C_1$-$C_6$ alkyl or $C_3$-$C_8$ cycloalkyl;

$R^6$ and $R^7$ are each independently H, $C_1$-$C_6$ alkyl or $C_3$-$C_8$ cycloalkyl or are taken together with the nitrogen atom to which they are attached to form a 4-, 5- or 6-membered saturated heterocyclic ring containing 1-2 nitrogen atoms or 1 nitrogen and 1 oxygen atom, said heterocyclic ring being optionally substituted by one or more $C_1$-$C_6$ alkyl or $C_3$-$C_8$ cycloalkyl groups;

$R^8$ is $C_1$-$C_6$ alkyl or $C_3$-$C_8$ cycloalkyl; and $R^9$ is pyridyl, benzyl or phenyl optionally substituted by halo, OH, $C_1$-$C_6$ alkyl and S—$C_1$-$C_6$ alkyl.

Wherein, for a compound of formula (Ia)

When $R^2$ is H and $R^1$ is biphenyl, said biphenyl must substituted and $R^4$ cannot be F, SO$_2$CH$_3$ or NR$^6$R$^7$ where $R^6$ and $R^7$ are taken together with the N atom to which they are attached to form a piperidine, pyrrolidine or morpholine ring; and When $R^2$ is H or OH, $R^1$ cannot be an unsubstituted phenoxyphenyl.

Wherein for a compound of formula (Ib)

When $R^2$ is H and $R^1$ is indole, said indole must be substituted and $R^4$ cannot be $C_1$-$C_6$ alkyl.

When $R^2$ is H and $R^1$ is indole, said indole cannot be substituted by phenyl at the 2 position.

When $R^2$ is H $R^1$ cannot be an unsubstituted indazole.

The invention also provides, as embodiment E2, a compound of formula (Ia), or a pharmaceutically acceptable salt thereof, or a pharmaceutically acceptable solvate of said compound or pharmaceutically acceptable salt, wherein $R^1$ and $R^2$ are as defined in embodiment E1.

The invention also provides, as embodiment E3, a compound of formula (Ib), or a pharmaceutically acceptable salt thereof, or a pharmaceutically acceptable solvate of said compound or pharmaceutically acceptable salt, wherein $R^1$ is as defined in embodiment E1.

The invention also provides, as embodiment E4, a compound of formula (Ic), or a pharmaceutically acceptable salt thereof, or a pharmaceutically acceptable solvate of said compound or pharmaceutically acceptable salt, wherein $R^1$ is as defined in embodiment E1.

The invention also provides, as embodiment E5, a compound, or a pharmaceutically acceptable salt thereof, or a pharmaceutically acceptable solvate of said compound or pharmaceutically acceptable salt, as defined in any one of embodiments E1, E2, E3, E4 or E5, in which $R^1$ is (i) indolyl, said indolyl being optionally substituted by 1 $R^3$ group and 1-3 $R^4$ groups or (ii) biphenyl, said biphenyl being optionally substituted by 1-3 $R^4$ groups.

In a preferred embodiment of the present invention are compounds of formula (Ia) and (Ic) Particularly preferred are compounds of formula (Ia)

$R^1$ is preferably indole or tetrahydroisoquinoline, optionally substituted by 1 $R^3$ group and 1-3 $R^4$ groups; or biphenyl, benzyl-phenyl & phenyl-thiophenyl, said group being optionally substituted by 1-3 $R^4$ groups;

more preferably $R^1$ is indole; or tetrahydroisoquinoline, optionally substituted by 1 $R^3$ group and 1-3 $R^4$ groups; or bi-phenyl substituted by 1-3 $R^4$ groups;

$R^2$ is preferably H

Preferably $R^3$ is —(CH$_2$)$_n$—Ar, wherein n is 0-4 and Ar is a phenyl group optionally substituted by 1-2 $R^4$ groups;

$R^4$ is preferably $C_1$-$C_6$ alkyl, $C_3$-$C_8$ cycloalkyl, halo, —CN, NR$^6$R$^7$, —SR$^5$, —SOR$^8$, —SO$_2$R$^8$, —COR$^5$, —OCOR$^5$, —COOR$^5$, —COR$^9$, —COOR$^9$, OR$^5$ where —COR$^9$ and —COOR$^9$, only attach via the N atom of $R^1$ $R^5$ is preferably H or $C_1$-$C_6$ alkyl;

More preferably $R^5$ is H or CH$_3$

A particularly preferred compound is any one of Examples 1-123, listed below, or a pharmaceutically acceptable salt thereof, or a pharmaceutically acceptable solvate of said compound or salt. Any two or more of these Examples may be combined to create a further embodiment of the invention.

Further preferred compounds include:

| NAME | Example number |
|---|---|
| 2-{[(1R*,2S*)-2-aminocyclohexyl]amino}-4-(1H-indol-4-ylamino)pyrido[4,3-d]pyrimidin-5(6H)-one | 1 |
| 2-{[(1R*,2S*)-2-aminocyclohexyl]amino}-4-({1-[3-(4-hydroxyphenyl)propyl]-1H-indol-4-yl}amino)pyrimidine-5-carboxamide | 2 |
| 2-{[1R*,2S*)-2-aminocyclohexyl]amino}-4-({1-[3-(3-hydroxyphenyl)propyl]-1H-indol-4-yl}amino)pyrimidine-5-carboxamide | 3 |
| 2-{[(1R*,2S*)-2-aminocyclohexyl]amino}-4-[(4'-hydroxybiphenyl-3-yl)amino]pyrimidine-5-carboxamide | 4 |
| 2-{[(1R*,2S*)-2-aminocyclohexyl]amino}-4-[(3'-hydroxybiphenyl-3-yl)amino]pyrimidine-5-carboxamide | 5 |
| 2-{[1R*,2S*)-2-aminocyclohexyl]amino-4-{[1-(4-methylbenzyl)-(1H-indol-4-yl]amino}pyrimidine-5-carboxamide | 6 |
| 2-{[(1R*,2S*)-2-aminocyclohexyl]amino-4-([1-[3-(3-methoxyphenyl)propyl]-1H-indol-4-yl}amino)pyrimidine-5-carboxamide | 7 |
| 2-{[(1R,2S)-2-aminocyclohexyl]amino-4-[(3'-hydroxybiphenyl-3-yl)amino]pyrimidine-5-carboxamide | 8 |
| 2-{[(1R*,2S*)-2-aminocyclohexyl]amino}-4-{[1-(3-methylbenzyl)-(1H-indol-4-yl]amino}pyrimidine-5-carboxamide | 9 |
| 2-{[1R,2S)-2-aminocyclohexyl]amino-4-[(1-benzyl-(1H-indol-4-yl)amino]pyrimidine-5-carboxamide | 10 |
| 2-{[(1R*,2S*)-2-aminocyclohexyl]amino}-4-[(3,5-dimethoxyphenyl)amino]-6-hydroxypyrimidine-5-carboxamide | 11 |
| 2-{[(1R*,2S*)-2-aminocyclohexyl]amino}-4-{[2-(pyridin-3-ylcarbonyl)-1,2,3,4-tetrahydroisoquinolin-7-yl]amino}pyrimidine-5-carboxamide | 12 |
| 2-{[(1R,2S)-2-aminocyclohexyl]amino-4-[(4'-hydroxybiphenyl-3-yl)amino]pyrimidine-5-carboxamide | 13 |
| 2-{[(1R*,2S*)-2-aminocyclohexyl]amino}-4-({1-[2-(4-hydroxyphenyl)ethyl]-1H-indol-4-yl}amino)pyrimidine-5-carboxamide | 14 |

-continued

| NAME | Example number |
|---|---|
| 2-{[(1R*,2S*)-2-aminocyclohexyl]amino-4-({1-[2-(4-methoxyphenyl)ethyl]-1H-indol-4-yl}amino)pyrimidine-5-carboxamide | 20 |
| 2-{[(1R*,2S*)-2-aminocyclohexyl]amino}-4-{{1-(4-chlorobenzyl)-(1H-indol-4-yl]amino}pyrimidine-5-carboxamide | 21 |
| 2-{[(1R*,2S*)-2-aminocyclohexyl]amino}-4-{{1-(-[2-(3-hydroxyphenyl)ethyl]-1H-indol-4-yl}amino)pyrimidine-5-carboxamide | 22 |
| 2-{[(1R*,2S*)-2-aminocyclohexyl]amino}-4-({1-[3-(2-methoxyphenyl)propyl]-1H-indol-4-yl}amino)pyrimidine-5-carboxamide | 23 |
| 5-{[(1R*,2S*)-2-aminocyclohexyl]amino}-7-(biphenyl-3-ylamino)imidazo[1,2-c]pyrimidine-8-carboxamide | 25 |
| 2-{[(1R*,2S*)-2-aminocyclohexyl]amino}-4-({1-[2-(2-hydroxyphenyl)ethyl]-1H-indol-4-yl}amino)pyrimidine-5-carboxamide | 26 |
| 2-{[(1R*,2S*)-2-aminocyclohexyl]amino}-4-{[2-(4-hydroxybenzoyl)-1,2,3,4-tetrahydroisoquinolin-7-yl]amino}pyrimidine-5-carboxamide | 27 |
| 2-{[(1R,2S)-2-aminocyclohexyl]amino}-4-{[1-(4-hydroxybenzyl)-(1H-indol-4-yl]amino}pyrimidine-5-carboxamide | 28 |
| 2-{[(1R*,2S*)-2-aminocyclohexyl]amino}-4-[(1-benzyl-(1H-indol-5-yl)amino]pyrimidine-5-carboxamide | 29 |
| 2-{[(1R,2S)-2-aminocyclohexyl]amino}-4-[4'-hydroxybiphenyl-3-yl)amino]pyrido[4,3-d]pyrimidin-5(6H)-one | 59 |

In a yet further preferred embodiment are compounds:

| NAME | Example number |
|---|---|
| 2-{[(1R*,2S*)-2-aminocyclohexyl]amino}-4-(1H-indol-4-ylamino)pyrido[4,3-d]pyrimidin-5(6H)-one | 1 |
| 2-{[(1R*,2S*)-2-aminocyclohexyl]amino}-4-({1-[3-(4-hydroxyphenyl)propyl]-1H-indol-4-yl}amino)pyrimidine-5-carboxamide | 2 |
| 2-{[(1R*,2S*)-2-aminocyclohexyl]amino}-4-[(4'-hydroxybiphenyl-3-yl)amino]pyrimidine-5-carboxamide | 4 |
| 2-{[(1R*,2S*)-2-aminocyclohexyl]amino}-4-{[1-(4-methylbenzyl)-(1H-indol-4-yl]amino}pyrimidine-5-carboxamide | 6 |
| 2-{[(1R*,2S*)-2-aminocyclohexyl]amino}-4-[(3,5-dimethoxyphenyl)amino-6-hydroxypyrimidine-5-carboxamide | 11 |
| 2-{[(1R*,2S*)-2-aminocyclohexyl]amino}-4-{[2-(pyridin-3-ylcarbonyl)-1,2,3,4-tetrahydroisoquinolin-7-yl]amino}pyrimidine-5-carboxamide | 12 |
| 2-{[(1R*,2S*)-2-aminocyclohexyl]amino}-4-({1-[2-(4-hydroxyphenyl)ethyl]-1H-indol-4-yl}amino)pyrimidine-5-carboxamide | 14 |
| 5-{[(1R*,2S*)-2-aminocyclohexyl]amino}-7-(biphenyl-3-ylamino)imidazo[1,2-c]pyrimidine-8-carboxamide | 25 |
| 2-{[(1R*,2S*)-2-aminocyclohexyl]amino}-4-{[2-(4-hydroxybenzoyl)-1,2,3,4-tetrahydroisoquinolin-7-yl]amino}pyrimidine-5-carboxamide | 27 |
| 2-{[(1R,2S)-2-aminocyclohexyl]amino}-4-[(4'-hydroxybiphenyl-3-yl)amino]pyrido[4,3-d]pyrimidin-5(6H)-one | 59 |

The present invention also provides: a method of treating a disease for which a SYK inhibitor is indicated, in a subject in need of such treatment, comprising administering to the subject a therapeutically effective amount of a compound of formula (Ia), (Ib) or (Ic), or a pharmaceutically acceptable salt thereof, or a pharmaceutically acceptable solvate of said compound or salt; the use of a compound of formula (Ia), (Ib) or (Ic), or a pharmaceutically acceptable salt thereof, or a pharmaceutically acceptable solvate of said compound or salt, for the manufacture of a medicament for treating a disease or condition for which a SYK inhibitor is indicated; a compound of formula (Ia), (Ib) or (Ic), or a pharmaceutically acceptable salt or solvate thereof, for use as a medicament; a compound of formula (Ia), (Ib) or (Ic), or a pharmaceutically acceptable salt thereof, or a pharmaceutically acceptable solvate of said compound or salt, for use in the treatment of a disease or condition for which a SYK inhibitor is indicated; a pharmaceutical composition comprising a compound of formula (Ia), (Ib) or (Ic), or a pharmaceutically acceptable salt thereof, or a pharmaceutically acceptable solvate of said compound or salt, and a pharmaceutically acceptable excipient; a pharmaceutical composition for the treatment of a disease or condition for which a SYK inhibitor is indicated, comprising a compound of formula (Ia), (Ib) or (Ic), or a pharmaceutically acceptable salt thereof, or a pharmaceutically acceptable solvate of said compound or salt.

The disease or condition for which a SYK inhibitor is indicated is preferably an allergic or respiratory condition such as allergic rhinitis, nasal congestion, rhinorrhea, perennial rhinitis, nasal inflammation, asthma of all types, chronic obstructive pulmonary disease (COPD), chronic or acute bronchoconstriction, chronic bronchitis, small airways obstruction, emphysema, chronic eosinophilic pneumonia, adult respiratory distress syndrome, exacerbation of airways hyper-reactivity consequent to other drug therapy, pulmonary vasulcar disease (including pulmonary arterial hypertension), acute lung injury, bronchiectasis, sinusitis, allergic conjunctivitis, idiopathic pulmonary fibrosis or atopic dermatitis, particularly asthma or allergic rhinitis or atopic dermatitis or allergic conjunctivitis.

Other diseases and conditions of interest are inflammation (including neuroinflammation), arthritis (including rheumatoid arthritis, spondyloarthropathies, systemic lupus erythematous arthritis, osteoarthritis and gouty arthritis), pain, fever, pulmonary sarcoisosis, silicosis, cardiovascular disease (including atherosclerosis, myocardial infarction, thrombosis, congestive heart failure and cardiac reperfusion injury), cardiomyopathy, stroke, ischaemia, reperfusion injury, brain edema, brain trauma, neurodegeneration, liver disease, inflammatory bowel disease (including Crohn's disease and ulcerative colitis), nephritis, retinitis, retinopathy, macular degeneration, glaucoma, diabetes (including type 1 and type 2 diabetes), dry eye disease, diabetic neurorpathy, viral and bacterial infection, myalgia, endotoxic shock, toxic shock syndrome, autoimmune disease, osteoporosis, multiple sclerosis, endometriosis, menstrual cramps, vaginitis, candidiasis, cancer, conjunctivitis, food allergy, fibrosis, obesity, muscular dystrophy, polymyositis, Alzheimer's disease, skin flushing, eczema, psoriasis, atopic dermatitis, rosacea, discoid lupus erythematosus, prurigo nodularis, alopecia and sunburn.

Types of asthma include atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis.

The treatment of asthma includes palliative treatment for the symptoms and conditions of asthma such as wheezing, coughing, shortness of breath, tightness in the chest, shallow or fast breathing, nasal flaring (nostril size increases with breathing), retractions (neck area and between or below the ribs moves inward with breathing), cyanosis (gray or bluish tint to skin, beginning around the mouth), runny or stuffy nose, and headache.

Conditions for which the compounds of the present invention are particularly indicated as suitable for treating include asthma, COPD, allergic rhinitis, chronic sinusitis, atopic dermatitis, psoriasis, rosacea, alopecia, allergic conjunctivitis and dry eye disease, Conditions for which the compounds of the present invention are particularly indicated as most suitable for treating are asthma, COPD, atopic dermatitis, psoriasis, allergic conjunctivitis, dry eye disease.

The present invention also provides any of the uses, methods or compositions as defined above wherein the compound of formula (Ia), (Ib) or (Ic), or pharmaceutically acceptable salt thereof, or pharmaceutically acceptable solvate of said compound or salt, is used in combination with another pharmacologically active compound, particularly one of the functionally-defined classes or specific compounds listed below. Generally, the compounds of the combination will be administered together as a formulation in association with one or more pharmaceutically acceptable excipients.

Suitable agents for use in combination therapy with a compound of formula (Ia), (Ib) or (Ic), or pharmaceutically acceptable salt thereof, or pharmaceutically acceptable solvate of said compound or salt, particularly in the treatment of respiratory disease, include:

a 5-lipoxygenase activating protein (FLAP) antagonist;

a leukotriene antagonist (LTRA) such as an antagonist of $LTB_4$, $LTC_4$, $LTD_4$, $LTE_4$, $CysLT_1$ or $CysLT_2$, e.g. montelukast or zafirlukast;

a histamine receptor antagonist, such as a histamine type 1 receptor antagonist or a histamine type 2 receptor antagonist, e.g. loratidine, fexofenadine, desloratidine, levocetirizine, methapyrilene or cetirizine;

an α1-adrenoceptor agonist or an α2-adrenoceptor agonist, e.g. phenylephrine, methoxamine, oxymetazoline or methylnorephrine;

a muscarinic M3 receptor antagonist, e.g. tiotropium or ipratropium;

a dual muscarinic M3 receptor antagononist/β2 agonist;

a PDE inhibitor, such as a PDE3 inhibitor, a PDE4 inhibitor or a PDE5 inhibitor, e.g. theophylline, sildenafil, vardenafil, tadalafil, ibudilast, cilomilast or roflumilast;

sodium cromoglycate or sodium nedocromil;

a cyclooxygenase (COX) inhibitor, such as a non-selective inhibitor (e.g. aspirin or ibuprofen) or a selective inhibitor (e.g. celecoxib or valdecoxib);

a glucocorticosteroid, e.g. fluticasone, mometasone, dexamethasone, prednisolone, budesonide, ciclesonide or beclamethasone;

an anti-inflammatory monoclonal antibody, e.g. infliximab, adalimumab, tanezumab, ranibizumab, bevacizumab or mepolizumab;

a β2 agonist, e.g. salmeterol, albuterol, salbutamol, fenoterol or formoterol, particularly a long-acting β2 agonist;

an intigrin antagonist, e.g. natalizumab;

an adhesion molecule inhibitor, such as a VLA-4 antagonist;

a kinin $B_1$ or $B_2$ receptor antagonist;

an immunosuppressive agent, such as an inhibitor of the IgE pathway (e.g. omalizumab) or cyclosporine;

a matrix metalloprotease (MMP) inhibitor, such as an inhibitor of MMP-9 or MMP-12;

a tachykinin $NK_1$, $NK_2$ or $NK_3$ receptor antagonist;

a protease inhibitor, such as an inhibitor of elastase, chymase or catheopsin G;

an adenosine $A_{2a}$ receptor agonist;

an adenosine $A_{2b}$ receptor antagonist;

a urokinase inhibitor;

a dopamine receptor agonist (e.g. ropinirole), particularly a dopamine D2 receptor agonist (e.g. bromocriptine);

a modulator of the NFκB pathway, such as an IKK inhibitor;

a further modulator of a cytokine signalling pathway such as an inhibitor of SYK kinase, syk kinase, p38 kinase, SPHK-1 kinase, Rho kinase, EGF-R or MK-2;

a mucolytic, mucokinetic or anti-tussive agent an antibiotic;

an antiviral agent;

a vaccine;

a chemokine;

an epithelial sodium channel (ENaC) blocker or Epithelial sodium channel (ENaC) inhibitor;

a nucleotide receptor agonist, such as a P2Y2 agonist;

a thromboxane inhibitor;

niacin;

a 5-lipoxygenase (5-LO) inhibitor, e.g. Zileuton;

an adhesion factor, such as VLAM, ICAM or ELAM;

a CRTH2 receptor ($DP_2$) antagonist;

a prostaglandin $D_2$ receptor ($DP_1$) antagonist;

a haematopoietic prostaglandin D2 synthase (HPGDS) inhibitor;

interferon-β;

a soluble human TNF receptor, e.g. Etanercept;

a HDAC inhibitor;

a phosphoinositotide 3-kinase gamma (PI3Kγ) inhibitor;

a phosphoinositide 3-kinase delta (PI3Kδ) inhibitor;

a CXCR-1 or a CXCR-2 receptor antagonist;

an IRAK-4 inhibitor; and a TLR-4 or TLR-9 inhibitor;

including the pharmaceutically acceptable salts of the specifically named compounds and the pharmaceutically acceptable solvates of said specifically named compounds and salts.

Besides being useful for human treatment, compounds of formula (Ia), (Ib) or (Ic) are also useful for veterinary treatment of companion animals, exotic animals and farm animals.

When used in the present application, the following abbreviations have the meanings set out below:

AcOH is acetic acid;

APCI (in relation to mass spectrometry) is atmospheric pressure chemical ionization;

BOP is (benzotriazol-1-yloxy)tris(dimethylamino)phosphonium hexafluorophosphate;

Calc is calculated;

$CDCl_3$ is deuterochloroform;

$CO_2Et$ is ethyl carboxylate;

DCC is N,N'-dicyclohexylcarbodiimide;

DCM is dichloromethane;

DEA is diethylamine;

DIAD is diisopropyl azodicarboxylate;

DIEA is N,N-diisopropylethylamine;

DIPEA is N,N-diisopropylethylamine;

DMA is N,N-dimethylacetamide;

DMF is N,N-dimethylformamide;

DMF-DMA is N,N-dimethylformamide dimethyl acetal;

DMSO is dimethyl sulphoxide;

DMSO-d$_6$ is fully deuterated dimethyl sulphoxide;
EDC/EDCl/EDC.Cl is N-(3-Dimethylaminopropyl)-N'-ethylcarbodiimide hydrochloride;
ES (in relation to mass spectrometry) is electrospray;
Et is ethyl;
EtOAc is ethyl acetate
Ex is Example;
h is hour(s);
HATU is N,N,N',N'-tetramethyl-O-(7-azabenzotriazol-1-yl) uronium hexafluorophosphate;
HBTU is N,N,N',N'-tetramethyl-O-(1H-benzotriazol-1-yl) uronium hexafluorophosphate;
HCl is hydrochloric acid;
1H NMR or $^1$H NMR is proton nuclear magnetic resonance;
HOAt is 1-hydroxy-7-azabenzotriazole;
HOBt is 1-hydroxybenzotriazole;
HPLC is high performance liquid chromatography;
$H_2SO_4$ is sulphuric acid;
IPA is isopropyl alcohol;
iPr is isopropyl;
$K_2CO_3$ is potassium carbonate;
$KMnO_4$ is potassium permanganate;
KOH is potassium hydroxide;
KOAc is potassium acetate;
LCMS is liquid chromatography mass spectrometry;
LRMS is low resolution mass spectrometry;
m-CPBA is meta-chloroperbenzoic acid
Me is methyl;
MeCN is acetonitrile;
MeOH is methanol;
MeOD-d$_4$ is fully deuterated methanol;
$MgSO_4$ is magnesium sulphate;
2-MeTHF is 2-methyltetrahydrofuran;
min is minute(s);
MS is mass spectroscopy;
NaCl is sodium chloride;
NaOH is sodium hydroxide;
NaH is sodium hydride;
NBS is N-bromosuccinimide;
NIS is N-iodosuccinimide;
NMM is 4-methylmorpholine;
NMP is N-methylpyrrolidine;
Obs is observed;
Pd(OAc)$_2$ is palladium(II)acetate;
RT is retention time;
SEM-Cl is (2-chloromethoxy-ethyl)-trimethyl-silane;
SPhos is 2-dicyclohexylphosphino-2',6'-dimethoxybiphenyl;
STAB is sodium (tri-acetoxy) borohydride;
TBTU is O-(benzotriazol-1-yl)-N,N,N',N'-tetramethyluronium tetrafluoroborate;
TEA is triethylamine;
TFA is trifluoroacetic acid;
THF is tetrahydrofuran;
tBME is 2-methoxy-2-methyl-propane;
p-TsOH is para-toluene sulfonic acid.

Unless otherwise defined herein, scientific and technical terms used in connection with the present invention have the meanings that are commonly understood by those of ordinary skill in the art.

The phrase "therapeutically effective" is intended to qualify the amount of compound or pharmaceutical composition, or the combined amount of active ingredients in the case of combination therapy. This amount or combined amount will achieve the goal of treating the relevant condition.

The term "treatment," as used herein to describe the present invention and unless otherwise qualified, means administration of the compound, pharmaceutical composition or combination to effect preventative, palliative, supportive, restorative or curative treatment. The term treatment encompasses any objective or subjective improvement in a subject with respect to a relevant condition or disease.

The term "preventive treatment," as used herein to describe the present invention, means that the compound, pharmaceutical composition or combination is administered to a subject to inhibit or stop the relevant condition from occurring in a subject, particularly in a subject or member of a population that is significantly predisposed to the relevant condition.

The term "palliative treatment," as used herein to describe the present invention, means that the compound, pharmaceutical composition or combination is administered to a subject to remedy signs and/or symptoms of a condition, without necessarily modifying the progression of, or underlying etiology of, the relevant condition.

The term "supportive treatment," as used herein to describe the present invention, means that the compound, pharmaceutical composition or combination is administered to a subject as a part of a regimen of therapy, but that such therapy is not limited to administration of the compound, pharmaceutical composition or combination. Unless otherwise expressly stated, supportive treatment may embrace preventive, palliative, restorative or curative treatment, particularly when the compounds or pharmaceutical compositions are combined with another component of supportive therapy.

The term "restorative treatment," as used herein to describe the present invention, means that the compound, pharmaceutical composition or combination is administered to a subject to modify the underlying progression or etiology of a condition. Non-limiting examples include an increase in forced expiratory volume in one second (FEV 1) for lung disorders, decreased rate of a decline in lung function over time, inhibition of progressive nerve destruction, reduction of biomarkers associated and correlated with diseases or disorders, a reduction in relapses, improvement in quality of life, reduced time spent in hospital during an acute exacerbation event and the like.

The term "curative treatment," as used herein to describe the present invention, means that compound, pharmaceutical composition or combination is administered to a subject for the purpose of bringing the disease or disorder into complete remission, or that the disease or disorder is undetectable after such treatment.

The term "selective", when used to describe a functionally-defined receptor ligand or enzyme inhibitor means selective for the defined receptor or enzyme subtype as compared with other receptor or enzyme subtypes in the same family. For instance, a selective PDE5 inhibitor is a compound which inhibits the PDE5 enzyme subtype more potently than any other PDE enzyme subtype. Such selectivity is preferably at least 2 fold (as measured using conventional binding assays), more preferably at least 10 fold, most preferably at least 100 fold.

The term "alkyl", alone or in combination, means an acyclic, saturated hydrocarbon group of the formula $C_nH_{2n+1}$ which may be linear or branched. Examples of such groups include methyl, ethyl, n-propyl, isopropyl, n-butyl, isobutyl, sec-butyl, tert-butyl, pentyl, iso-amyl and hexyl. Unless otherwise specified, an alkyl group comprises from 1 to 6 carbon atoms.

The carbon atom content of alkyl and various other hydrocarbon-containing moieties is indicated by a prefix designating a lower and upper number of carbon atoms in the moiety, that is, the prefix $C_i$-$C_j$ indicates a moiety of the integer "i" to the integer "j" carbon atoms, inclusive. Thus, for example, $C_1$-$C_6$ alkyl refers to alkyl of one to six carbon atoms, inclusive.

The term "hydroxy," as used herein, means an OH radical.

The heterocycle which forms part of the definition of $R^1$ is an aromatic heterocycle and is attached via a ring carbon atom. When substituted, the substituent may be located on a ring carbon atom (in all cases) or a ring nitrogen atom with an appropriate valency (if the substituent is joined through a carbon atom). The heterocycle is aromatic and is therefore necessarily a fused bicycle. Specific examples include benzofuranyl, benzothienyl, indolyl, benzimidazolyl, indazolyl and benzotriazolyl.

The term "cycloalkyl" means a means a monocyclic, saturated hydrocarbon group of the formula $C_nH_{2n-1}$. Examples include cyclopropyl, cyclobutyl, cyclopentyl, cyclohexyl, and cycloheptyl. Unless otherwise specified, a cycloalkyl group comprises from 3 to 8 carbon atoms.

The term "oxo" means a doubly bonded oxygen.

The term "alkoxy" means a radical comprising an alkyl radical that is bonded to an oxygen atom, such as a methoxy radical. Examples of such radicals include methoxy, ethoxy, propoxy, isopropoxy, butoxy and tert-butoxy.

The term "halo" means, fluoro, chloro, bromo or iodo.

As used herein, the terms "co-administration", "co-administered" and "in combination with", referring to a combination of a compound of formula (Ia), (Ib) or (Ic) and one or more other therapeutic agents, includes the following:

simultaneous administration of such a combination of a compound of formula (Ia), (Ib) or (Ic) and a further therapeutic agent to a patient in need of treatment, when such components are formulated together into a single dosage form which releases said components at substantially the same time to said patient, substantially simultaneous administration of such a combination of a compound of formula (I) and a further therapeutic agent to a patient in need of treatment, when such components are formulated apart from each other into separate dosage forms which are taken at substantially the same time by said patient, whereupon said components are released at substantially the same time to said patient, sequential administration of such a combination of a compound of formula (Ia), (Ib) or (Ic) and a further therapeutic agent to a patient in need of treatment, when such components are formulated apart from each other into separate dosage forms which are taken at consecutive times by said patient with a significant time interval between each administration, whereupon said components are released at substantially different times to said patient; and sequential administration of such a combination of a compound of formula (Ia), (Ib) or (Ic) and a further therapeutic agent to a patient in need of treatment, when such components are formulated together into a single dosage form which releases said components in a controlled manner.

The term 'excipient' is used herein to describe any ingredient other than a compound of formula (Ia), (Ib) or (Ic). The choice of excipient will to a large extent depend on factors such as the particular mode of administration, the effect of the excipient on solubility and stability, and the nature of the dosage form. The term "excipient" encompasses diluent, carrier or adjuvant.

One way of carrying out the invention is to administer a compound of formula (Ia), (Ib) or (Ic) in the form of a prodrug. Thus, certain derivatives of a compound of formula (Ia), (Ib) or (Ic) which may have little or no pharmacological activity themselves can, when administered into or onto the body, be converted into a compound of formula (Ia), (Ib) or (Ic) having the desired activity, for example by hydrolytic cleavage, particularly hydrolytic cleavage promoted by an esterase or peptidase enzyme. Such derivatives are referred to as 'prodrugs'. Further information on the use of prodrugs may be found in 'Pro-drugs as Novel Delivery Systems', Vol. 14, ACS Symposium Series (T. Higuchi and W. Stella) and 'Bioreversible Carriers in Drug Design', Pergamon Press, 1987 (Ed. E. B. Roche, American Pharmaceutical Association). Reference can also be made to Nature Reviews/Drug Discovery, 2008, 7, 355 and Current Opinion in Drug Discovery and Development, 2007, 10, 550.

Prodrugs in accordance with the invention can, for example, be produced by replacing appropriate functionalities present in the compounds of formula (Ia), (Ib) or (Ic) with certain moieties known to those skilled in the art as 'pro-moieties' as described, for example, in 'Design of Prodrugs' by H. Bundgaard (Elsevier, 1985).

Thus, a prodrug in accordance with the invention is (a) an ester or amide derivative of a carboxylic acid in a compound of formula (Ia), (Ib) or (Ic); (b) an ester, carbonate, carbamate, phosphate or ether derivative of a hydroxyl group in a compound of formula (Ia), (Ib) or (Ic); (c) an amide, imine, carbamate or amine derivative of an amino group in a compound form formula (I); (d) a thioester, thiocarbonate, thiocarbamate or sulphide derivatives of a thiol group in a compound of formula (Ia), (Ib) or (Ic); or (e) an oxime or imine derivative of a carbonyl group in a compound of formula (Ia), (Ib) or (Ic).

Some specific examples of prodrugs in accordance with the invention include:

(i) where the compound of formula (Ia), (Ib) or (Ic) contains a carboxylic acid functionality (—COOH), an ester thereof, such as a compound wherein the hydrogen of the carboxylic acid functionality of the compound of formula (Ia), (Ib) or (Ic) is replaced by $C_1$-$C_8$ alkyl (e.g. ethyl) or ($C_1$-$C_8$ alkyl)C(=O)OCH$_2$— (e.g. $^t$BuC(=O)OCH$_2$—);

(ii) where the compound of formula (Ia), (Ib) or (Ic) contains an alcohol functionality (—OH), an ester thereof, such as a compound wherein the hydrogen of the alcohol functionality of the compound of formula (Ia), (Ib) or (Ic) is replaced by —CO($C_1$-$C_8$ alkyl) (e.g. methylcarbonyl) or the alcohol is esterified with an amino acid;

(iii) where the compound of formula (Ia), (Ib) or (Ic) contains an alcohol functionality (—OH), an ether thereof, such as a compound wherein the hydrogen of the alcohol functionality of the compound of formula (Ia), (Ib) or (Ic) is replaced by ($C_1$-$C_8$ alkyl)C(=O)OCH$_2$— or —CH$_2$OP(=O)(OH)$_2$;

(iv) where the compound of formula (Ia), (Ib) or (Ic) contains an alcohol functionality (—OH), a phosphate thereof, such as a compound wherein the hydrogen of the alcohol functionality of the compound of formula (Ia), (Ib) or (Ic) is replaced by —P(=O)(OH)$_2$ or —P(=O)(ONa)$_2$ or —P(=O)(O$^-$)$_2$Ca$^{2+}$;

(v) where the compound of formula (Ia), (Ib) or (Ic) contains a primary or secondary amino functionality (—NH$_2$ or —NHR where R≠H), an amide thereof, for example, a compound wherein, as the case may be, one or both hydrogens of the amino functionality of the compound of formula (Ia), (Ib) or (Ic) is/are replaced by $(C_1$-$C_{10})$ alkanoyl, —COCH$_2$NH$_2$ or the amino group is derivatised with an amino acid;

(vi) where the compound of formula (Ia), (Ib) or (Ic) contains a primary or secondary amino functionality (—NH$_2$ or —NHR where R≠H), an amine thereof, for example, a compound wherein, as the case may be, one or both hydrogens of the amino functionality of the compound of formula (Ia), (Ib) or (Ic) is/are replaced by —CH$_2$OP(=O)(OH)$_2$.

Certain compounds of formula (Ia), (Ib) or (Ic) may themselves act as prodrugs of other compounds of formula (Ia), (Ib) or (Ic). It is also possible for two compounds of formula (Ia), (Ib) or (Ic) to be joined together in the form of a prodrug. In certain circumstances, a prodrug of a compound of formula (Ia), (Ib) or (Ic) may be created by internally linking two functional groups in a compound of formula (Ia), (Ib) or (Ic), for instance by forming a lactone.

References below to compounds of formula (Ia), (Ib) or (Ic) are taken to include the compounds themselves and prodrugs thereof. The invention includes such compounds of formula (Ia), (Ib) or (Ic) as well as pharmaceutically acceptable salts of such compounds and pharmaceutically acceptable solvates of said compounds and salts.

Pharmaceutically acceptable salts of the compounds of formula (Ia), (Ib) or (Ic) include acid addition and base salts.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, naphatlene-1,5-disulfonic acid and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002).

Pharmaceutically acceptable salts of compounds of formula (Ia), (Ib) or (Ic) may be prepared by one or more of three methods:

(i) by reacting the compound of formula (Ia), (Ib) or (Ic) with the desired acid or base;
(ii) by removing an acid- or base-labile protecting group from a suitable precursor of the compound of formula (Ia), (Ib) or (Ic) or by ring-opening a suitable cyclic precursor, for example, a lactone or lactam, using the desired acid or base; or
(iii) by converting one salt of the compound of formula (Ia), (Ib) or (Ic) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (Ia), (Ib) or (Ic), and pharmaceutically acceptable salts thereof, may exist in unsolvated and solvated forms. The term 'solvate' is used herein to describe a molecular complex comprising the compound of formula (Ia), (Ib) or (Ic), or a pharmaceutically acceptable salt thereof, and one or more pharmaceutically acceptable solvent molecules, for example, ethanol. The term 'hydrate' may be employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order (glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order (melting point').

The compounds of formula (Ia), (Ib) or (Ic) may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

Hereinafter all references to compounds of formula (Ia), (Ib) or (Ic) include references to pharmaceutically acceptable salts, solvates, multi-component complexes and liquid crystals thereof and to solvates, multi-component complexes and liquid crystals of pharmaceutically acceptable salts thereof.

The compounds of formula (Ia), (Ib) or (Ic) contain a cis-2-aminocyclohexylamino group. The two amino moieties of this group have a cis relationship about the cyclohexyl ring and this is an essential feature of the invention; the invention does not include compounds having a trans relationship of amino groups about the cyclohexyl ring. This cis-2-aminocyclohexylamino group may exist in one of two enantiomeric forms. The present invention relates to both enantiomeric forms, the racemic form and mixtures of the two enantiomers in any ratio. The 1 R,2S form is the preferred enantiomer for each of the embodiments E1, E2, E3, E4 and E5 described above. The present invention also includes In the Examples section, the racemic form is designated by the IUPAC nomenclature (1R*,1S*) and the preferred enantiomer by the usual designation (1R,1S). Further preferred compounds of the invention are the (1R, 1S) forms of each of the Examples which are described below in racemic form.

Further stereoisomerism may result from the presence of an asymmetric centre in the R$^1$ group—all such further stereoisomers individually, and mixtures thereof, are within the scope of the invention.

The compounds of formula (Ia), (Ib) or (Ic) may exhibit polymorphism and/or one or more further kinds of isomerism (e.g. geometric or tautomeric isomerism). The compounds of formula (Ia), (Ib) or (Ic) may also be isotopically labelled. Such variation is implicit to the compounds of formula (Ia), (Ib) or (Ic) defined as they are by reference to their structural features and therefore within the scope of the invention.

Where a compound of formula (Ia), (Ib) or (Ic) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (Ia), (Ib) or (Ic) containing, for example, an imino, keto, or oxime group, or so-called valence tautomerism in compounds which contain an aromatic moiety. It follows that a single compound may exhibit more than one type of isomerism.

The pharmaceutically acceptable salts of compounds of formula (Ia), (Ib) or (Ic) may also contain a counterion which is optically active (e.g. d-lactate or l-lysine) or racemic (e.g. dl-tartrate or dl-arginine).

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of formula (Ia), (Ib) or (Ic) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of formula (Ia), (Ib) or (Ic) (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. Chiral chromatography using sub- and supercritical fluids may be employed. Methods for chiral chromatography useful in some embodiments of the present invention are known in the art (see, for example, Smith, Roger M., Loughborough University, Loughborough, UK; Chromatographic Science Series (1998), 75 (Supercritical Fluid Chromatography with Packed Columns), pp.

223-249 and references cited therein). In some relevant examples herein, columns were obtained from Chiral Technologies, Inc, West Chester, Pa., USA, a subsidiary of Daicel® Chemical Industries, Ltd., Tokyo, Japan.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

The present invention includes all pharmaceutically acceptable isotopically-labelled compounds of formula (Ia), (Ib) or (Ic) wherein one or more atoms are replaced by atoms having the same atomic number, but an atomic mass or mass number different from the atomic mass or mass number which predominates in nature. Isotopically-labelled compounds of formula (Ia), (Ib) or (Ic) can generally be prepared by conventional techniques known to those skilled in the art or by processes analogous to those described in the accompanying Examples and Preparations using an appropriate isotopically-labelled reagent in place of the non-labelled reagent previously employed. In particular, hydrogen atoms may be replaced by deuterium atoms since such deuterated compounds are sometimes more resistant to metabolism.

Also included within the scope of the invention are active metabolites of compounds of formula (Ia), (Ib) or (Ic), that is, compounds formed in vivo upon administration of the drug, often by oxidatation or dealkylation. Some examples of metabolites in accordance with the invention include
(i) where the compound of formula (Ia), (Ib) or (Ic) contains a methyl group, an hydroxymethyl derivative thereof (—CH$_3$→—CH$_2$OH):

(ii) where the compound of formula (Ia), (Ib) or (Ic) contains an alkoxy group, an hydroxy derivative thereof (—OR→—OH);
(iii) where the compound of formula (Ia), (Ib) or (Ic) contains a tertiary amino group, a secondary amino derivative thereof (—NRR'→—NHR or —NHR');
(iv) where the compound of formula (Ia), (Ib) or (Ic) contains a secondary amino group, a primary derivative thereof (—NHR→—NH$_2$);
(v) where the compound of formula (Ia), (Ib) or (Ic) contains a phenyl moiety, a phenol derivative thereof (-Ph→-PhOH); and
(vi) where the compound of formula (Ia), (Ib) or (Ic) contains an amide group, a carboxylic acid derivative thereof (—CONH$_2$→COOH).

For administration to human patients, the total daily dose of a compound of formula (Ia), (Ib) or (Ic) is typically in the range of 0.01 mg to 500 mg depending, of course, on the mode of administration. In another embodiment of the present invention, the total daily dose of a compound of formula (Ia), (Ib) or (Ic) is typically in the range of 0.1 mg to 300 mg. In yet another embodiment of the present invention, the total daily dose of a compound of formula (Ia), (Ib) or (Ic) is typically in the range of 1 mg to 30 mg. The total daily dose may be administered in single or divided doses and may, at the physician's discretion, fall outside of the typical range given herein. These dosages are based on an average human subject having a weight of about 65 kg to 70 kg. The physician will readily be able to determine doses for subjects whose weight falls outside this range, such as infants and the elderly.

In the case of dry powder inhalers and aerosols, the dosage unit is determined by means of a prefilled capsule, blister or pocket or by a system that utilises a gravimetrically fed dosing chamber. Units in accordance with the invention are typically arranged to administer a metered dose or "puff" containing from 1 to 5000 µg of drug. The overall daily dose will typically be in the range 1 µg to 20 mg which may be administered in a single dose or, more usually, as divided doses throughout the day.

A compound of formula (Ia), (Ib) or (Ic) can be administered per se, or in the form of a pharmaceutical composition, which, as active constituent contains an efficacious dose of at least one compound of the invention, in addition to customary pharmaceutically innocuous excipients and/or additives.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

Compounds of formula (Ia), (Ib) or (Ic) may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Compounds of formula (Ia), (Ib) or (Ic) may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %. In one embodiment of the present invention, the disintegrant will comprise from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate. Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet. Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %. In one embodiment of the present invention, lubricants comprise from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. Formulations of tablets are discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (Ia), (Ib) or (Ic), a film-forming polymer, a binder, a solvent, a humectant, a plasticiser, a stabiliser or emulsifier, a viscosity-modifying agent and a solvent. Some components of the formulation may perform more than one function. The film-forming polymer may be selected from natural polysaccharides, proteins, or synthetic hydrocolloids and is typically present in the range 0.01 to 99 weight %, more typically in the range 30 to 80 weight %. Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents. Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release includes delayed, sustained, pulsed, controlled, targeted and programmed release. Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO-A-00/35298.

Compounds of formula (Ia), (Ib) or (Ic) may also be administered directly into the blood stream, into muscle, or into an internal organ. Such parenteral administration includes intravenous, intraarterial, intraperitoneal, intrathecal, intraventricular, intraurethral, intrasternal, intracranial, intramuscular and subcutaneous administration. Suitable devices for parenteral administration include needle (including microneedle) injectors, needle-free injectors and infusion techniques.

The compounds of the present invention are particularly favoured for non-systemic or topical delivery, through which they are administered locally to the surface of the specific organ in order to deliver targeted efficacy and minimal systemic free drug concentrations. This is in contrast to more standard delivery systems (e.g. oral and intravenous administration) where high systemic drug concentrations are required for efficacy. Such non-systemic or topical delivery provides compounds with particular advantages regarding safety and toleration, compared to oral medications. Taking a medicament systemically can lead to undesirable adverse effects, which may be unacceptable for non-life-threatening diseases. This can be avoided by delivery directly to the target organ. Particularly advantageous non-systemic delivery forms are through topical routes, particularly intranasal, inhaled, dermal or transdermal delivery to the target organ.

Compounds of formula (Ia), (Ib) or (Ic) can be administered topically to the skin or mucosa, that is, dermally or transdermally, in the form of a cream, ointment, paste, gel, suspension and solution.

The compounds of formula (Ia), (Ib) or (Ic) can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin. For intranasal use, the powder may comprise a bioadhesive agent, for example, chitosan or cyclodextrin. Intranasal delivery is the preferred route of administration for the compounds of the present invention.

The pressurised container, pump, spray, atomizer, or nebuliser contains a solution or suspension of the compound of formula (Ia), (Ib) or (Ic) comprising, for example, ethanol, aqueous ethanol, or a suitable alternative agent for dispersing, solubilising, or extending release of the compound, a propellant as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as 1-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (Ia), (Ib) or (Ic), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for intranasal administration. Formulations for intranasal administration may be formulated to be immediate and/or modified release using, for example, PGLA. Modified release includes delayed, sustained, pulsed, controlled, targeted and programmed release.

Compounds of formula (Ia), (Ib) or (Ic) may also be administered directly to the eye or ear, typically in the form of drops of a micronised suspension or solution in isotonic, pH-adjusted, sterile saline. Other forms include cream, ointment, paste and gel.

Compounds of formula (Ia), (Ib) or (Ic) may be combined with soluble macromolecular entities, such as cyclodextrin and suitable derivatives thereof or polyethylene glycol-containing polymers, in order to improve their solubility, dissolution rate, taste, bioavailability and/or stability when using any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in international patent publications WO-A-91/11172, WO-A-94/02518 and WO-A-98/55148.

Inasmuch as it may desirable to administer a combination of active compounds, for example, for the purpose of treating a particular disease or condition, it is within the scope of the present invention that two or more pharmaceutical compositions, at least one of which contains a compound of formula (Ia), (Ib) or (Ic), may conveniently be combined in the form of a kit suitable for coadministration of the compositions. Thus, a kit of the invention comprises two or more separate pharmaceutical compositions, at least one of which contains a compound of formula (Ia), (Ib) or (Ic), and means for separately retaining said compositions, such as a container, divided bottle, or divided foil packet. An example of such a kit is the familiar blister pack used for the packaging of tablets, capsules and the like. Such a kit is particularly suitable for administering different dosage forms, for example, oral and parenteral, for administering separate compositions at different dosage intervals, or for titrating the separate compositions against one another. To assist compliance, the kit typically comprises directions for administration and may be provided with a so-called memory aid.

The following Examples are preferred compounds of formula (Ia), (Ib) or (Ic):

| NAME | Example number |
|---|---|
| 2-{[(1R*,2S*)-2-aminocyclohexyl]amino}-4-(1H-indol-4-ylamino)pyrido[4,3-d]pyrimidin-5(6H)-one | 1 |
| 2-{[(1R*,2S*)-2-aminocyclohexyl]amino}-4-({1-[3-(4-hydroxyphenyl)propyl]-1H-indol-4-yl}amino)pyrimidine-5-carboxamide | 2 |
| 2-{[(1R*,2S*)-2-aminocyclohexyl]amino}-4-({1-[3-(3-hydroxyphenyl)propyl]-1H-indol-4-yl}amino)pyrimidine-5-carboxamide | 3 |
| 2-{[(1R*,2S*)-2-aminocyclohexyl]amino}-4-[(4'-hydroxybiphenyl-3-yl)amino]pyrimidine-5-carboxamide | 4 |
| 2-{[(1R*,2S*)-2-aminocyclohexyl]amino}-4-[(3'-hydroxybiphenyl-3-yl)amino]pyrimidine-5-carboxamide | 5 |
| 2-{[(1R*,2S*)-2-aminocyclohexyl]amino}-4-{[1-(4-methylbenzyl)-(1H-indol-4-yl]amino}pyrimidine-5-carboxamide | 6 |
| 2-{[(1R*,2S*)-2-aminocyclohexyl]amino}-4-({1-[3-(3-methoxyphenyl)propyl]-1H-indol-4-yl}amino)pyrimidine-5-carboxamide | 7 |
| 2-{[(1R,2S)-2-aminocyclohexyl]amino}-4-[(3'-hydroxybiphenyl-3-yl)amino]pyrimidine-5-carboxamide | 8 |
| 2-{[(1R*,2S*)-2-aminocyclohexyl]amino}-4-{[1-(3-methylbenzyl)-(1H-indol-4-yl]amino}pyrimidine-5-carboxamide | 9 |
| 2-{[(1R,2S)-2-aminocyclohexyl]amino}-4-[(1-benzyl-(1H-indol-4-yl)amino]pyrimidine-5-carboxamide | 10 |
| 2-{[(1R*,2S*)-2-aminocyclohexyl]amino}-4-[(3,5-dimethoxyphenyl)amino]-6-hydroxypyrimidine-5-carboxamide | 11 |
| 2-{[(1R*,2S*)-2-aminocyclohexyl]amino}-4-{[2-(pyridin-3-ylcarbonyl)-1,2,3,4-tetrahydroisoquinolin-7-yl]amino}pyrimidine-5-carboxamide | 12 |
| 2-{[(1R,2S)-2-aminocyclohexyl]amino}-4-[(4'-hydroxybiphenyl-3-yl)amino]pyrimidine-5-carboxamide | 13 |
| 2-{[(1R*,2S*)-2-aminocyclohexyl]amino}-4-({1-[2-(4-hydroxyphenyl)ethyl]-1H-indol-4-yl}amino)pyrimidine-5-carboxamide | 14 |
| 2-{[(1R*,2S*)-2-aminocyclohexyl]amino}-4-{[2-(cyclobutylcarbonyl)-1,2,3,4-tetrahydroisoquinolin-7-yl]amino}pyrimidine-5-carboxamide | 15 |
| 2-{[(1R*,2S*)-2-aminocyclohexyl]amino}-4-{[2-(phenylacetyl)-1,2,3,4-tetrahydroisoquinolin-7-yl]amino}pyrimidine-5-carboxamide | 16 |
| 2-{[(1R*,2S*)-2-aminocyclohexyl]amino}-4-(3'-methylbiphenyl-3-yl)amino]pyrimidine-5-carboxamide | 17 |
| 2-{[(1R*,2S*)-2-aminocyclohexyl]amino}-4-({1-[3-(4-methoxyphenyl)propyl]-1H-indol-4-yl}amino)pyrimidine-5-carboxamide | 18 |
| 2-{[(1R*,2S*)-2-aminocyclohexyl]amino}-4-(2-propionyl-1,2,3,4-tetrahydroisoquinolin-7-yl)amino]pyrimidine-5-carboxamide | 19 |
| 2-{[(1R*,2S*)-2-aminocyclohexyl]amino}4-({1-[2-(4-methoxyphenyl)ethyl]-1H-indol-4-yl}amino)pyrimidine-5-carboxamide | 20 |
| 2-{[(1R*,2S*)-2-aminocyclohexyl]amino}-4-{[1-(4-chlorobenzyl)-(1H-indol-4-yl]amino}pyrimidine-5-carboxamide | 21 |
| 2-{[(1R*,2S*)-2-aminocyclohexyl]amino}-4-({1-[2-(3-hydroxyphenyl)ethyl]-1H-indol-4-yl}amino)pyrimidine-5-carboxamide | 22 |
| 2-{[(1R*,2S*)-2-aminocyclohexyl]amino}-4-({1-[3-(2-methoxyphenyl)propyl]-1H-indol-4-yl}amino)pyrimidine-5-carboxamide | 23 |
| 2-{[(1R*,2S*)-2-aminocyclohexyl]amino}-4-[(2-isonicotinoyl-1,2,3,4-tetrahydroisoquinolin-7-yl)amino]pyrimidine-5-carboxamide | 24 |
| 5-{[(1R*,2S*)-2-aminocyclohexyl]amino}-7-(biphenyl-3-ylamino)imidazo[1,2-c]pyrimidine-8-carboxamide | 25 |
| 2-{[(1R*,2S*)-2-aminocyclohexyl]amino}-4-({1-[2-(2-hydroxyphenyl)ethyl]-1H-indol-4-yl}amino)pyrimidine-5-carboxamide | 26 |
| 2-{[(1R*,2S*)-2-aminocyclohexyl]amino}-4-{[2-(4-hydroxybenzoyl)-1,2,3,4-tetrahydroisoquinolin-7-yl]amino}pyrimidine-5-carboxamide | 27 |
| 2-{[(1R,2S)-2-aminocyclohexyl]amino}-4-{[1-(4-hydroxybenzyl)-(1H-indol-4-yl]amino}pyrimidine-5-carboxamide | 28 |
| 2-{[(1R*,2S*)-2-aminocyclohexyl]amino}-4-[(1-benzyl-(1H-indol-5-yl)amino]pyrimidine-5-carboxamide | 29 |
| 2-{[(1R,2S)-2-aminocyclohexyl]amino}-4-({1-[2-(4-hydroxyphenyl)ethyl]-1H-indol-4-yl}amino)pyrimidine-5-carboxamide | 30 |
| 2-{[(1R,2S)-2-aminocyclohexyl]amino}-4-({1-[3-(4-hydroxyphenyl)propyl]-1H-indol-4-yl}amino)pyrimidine-5-carboxamide | 31 |
| 2-{[(1R,2S)-2-aminocyclohexyl]amino}-4-{[1-(3-hydroxybenzyl)-(1H-indol-4-yl]amino}pyrimidine-5-carboxamide | 32 |
| 2-{[(1R*,2S*)-2-aminocyclohexyl]amino}-4-{[1-(3-phenylpropyl)-(1H-indol-4-yl]aminolpyrimidine-5-carboxamide | 33 |
| 2-{[(1R*,2S*)-2-aminocyclohexyl]amino}-4-({1-[2-(3-methoxyphenyl)ethyl]-1H-indol-4-yl}amino)pyrimidine-5-carboxamide | 34 |
| 2-{[(1R,2S)-2-aminocyclohexyl]amino}-4-({1-[2-(4-methoxyphenyl)ethyl-1H-indol-4-yl}amino)pyrimidine-5-carboxamide | 35 |
| methyl 7-[(2-{[(1R*,2S*)-2-aminocyclohexyl]amino}-5-carbamoylpyrimidin-4-yl)amino]-3,4-dihydroisoquinoline-2(1H)-carboxylate | 36 |
| 2-{[(1R*,2S*)-2-aminocyclohexyl]amino}-4-({1-[2-(2-methoxyphenyl)ethyl]-1H-indol-4-yl}amino)pyrimidine-5-carboxamide | 37 |
| ethyl 7-[(2-{[(1R*,2S*)-2-aminocyclohexyl]amino}-5-carbamoylpyrimidin-4-yl)amino]-3,4-dihydroisoquinoline-2(1H)-carboxylate | 38 |
| 2-{[(1R*,2S*)-2-aminocyclohexyl]amino}-4-{[1-(2-phenylethyl)-(1H-indol-4-yl]amino}pyrimidine-5-carboxamide | 39 |
| 2-{[(1R*,2S*)-2-aminocyclohexyl]amino}-4-{[2-(ethylsulfonyl)-1,2,3,4-tetrahydroisoquinolin-7-yl]amino}pyrimidine-5-carboxamide | 40 |
| 2-{[(1R,2S)-2-aminocyclohexyl]amino}-4-({1-[3-(4-methoxyphenyl)propyl]-1H-indol-4-yl}amino)pyrimidine-5-carboxamide | 41 |
| 2-{[(1R*,2S*)-2-aminocyclohexyl]amino}-4-[(1-benzyl-(1H-indol-6-yl)amino]pyrimidine-5-carboxamide | 42 |

| NAME | Example number |
|---|---|
| 2-{[(1R*,2S*)-2-aminocyclohexyl]amino}-4-{[2-(2-hydroxybenzoyl)-1,2,3,4-tetrahydroisoquinolin-7-yl]amino}pyrimidine-5-carboxamide | 43 |
| 2-{[(1R*,2S*)-2-aminocyclohexyl]amino}-4-[(4'-chloro-3-hydroxybiphenyl-3-yl)amino]pyrimidine-5-carboxamide | 44 |
| phenyl 7-[(2-{[(1R*,2S*)-2-aminocyclohexyl]amino}-5-carbamoylpyrimidin-4-yl)amino]-3,4-dihydroisoquinoline-2(1H)-carboxylate | 45 |
| 2-{[(1R*,2S*)-2-aminocyclohexyl]amino}-4-{[2-(3-hydroxybenzoyl)-1,2,3,4-tetrahydroisoquinolin-7-yl]amino}pyrimidine-5-carboxamide | 46 |
| 2-{[(1R*,2S*)-2-aminocyclohexyl]amino}-4-[(2-benzoyl-1,2,3,4-tetrahydroisoquinolin-7-yl)amino]pyrimidine-5-carboxamide | 47 |
| 2-{[(1R*,2S*)-2-aminocyclohexyl]amino}-4-({2-[3-(methylthio)benzoyl]-1,2,3,4-tetrahydroisoquinolin-7-yl}amino)pyrimidine-5-carboxamide | 48 |
| 2-{[(1R*,2S*)-2-aminocyclohexyl]amino}-4-{[2-(benzylsulfonyl)-1,2,3,4-tetrahydroisoquinolin-7-yl]amino}pyrimidine-5-carboxamide | 49 |
| isopropyl 7-[(2-{[(1R*,2S*)-2-aminocyclohexyl]amino}-5-carbamoylpyrimidin-4-yl)amino]-3,4-dihydroisoquinoline-2(1H)-carboxylate | 50 |
| 2-{[(1R*,2S*)-2-aminocyclohexyl]amino}-4-[(4'-chlorobiphenyl-3-yl)amino]pyrimidine-5-carboxamide | 51 |
| 2-{[(1R*,2S*)-2-aminocyclohexyl]amino}-4-({1-[3-(methylthio)benzyl]-1H-indol-4-yl}amino)pyrimidine-5-carboxamide | 52 |
| 4-[(acetyl-1,2,3,4-tetrahydroisoquinolin-7-yl)amino]-2-{[(1R*,2S*)-2-aminocyclohexyl]amino}pyrimidine-5-carboxamide | 53 |
| 2-{[(1R,2S)-2-aminocyclohexyl]amino}-4-{[1-(2-hydroxybenzyl)-(1H-indol-4-yl]amino}pyrimidine-5-carboxamide | 54 |
| benzyl 7-[(2-{[(1R*,2S*)-2-aminocyclohexyl]amino}-5-carbamoylpyrimidin-4-yl)amino]-3,4-dihydroisoquinoline-2(1H)-carboxylate | 55 |
| 2-{[(1R*,2S*)-2-aminocyclohexyl]amino}-4-{[2-(3-fluorobenzoyl)-1,2,3,4-tetrahydroisoquinolin-7-yl]amino}pyrimidine-5-carboxamide | 56 |
| cyclopropyl 7-[(2-{[(1R*,2S*)-2-aminocyclohexyl]amino}-5-carbamoylpyrimidin-4-yl)amino]-3,4-dihydroisoquinoline-2(1H)-carboxylate | 57 |
| 2-{[(1R*,2S*)-2-aminocyclohexyl]amino}-4-{[2-(methylsulfonyl)-1,2,3,4-tetrahydroisoquinolin-7-yl]amino}pyrimidine-5-carboxamide | 58 |
| 2-{[(1R,2S)-2-aminocyclohexyl]amino}-4-[(4'-hydroxybiphenyl-3-yl)amino]pyrido[4,3-d]pyrimidin-5(6H)-one | 59 |
| 2-{[(1R*,2S*)-2-aminocyclohexyl]amino}-4-{[1-(2-fluorobenzyl)-(1H-indol-4-yl]amino}pyrimidine-5-carboxamide | 60 |
| 2-{[(1R*,2S*)-2-aminocyclohexyl]amino}-4-{[2-(cyclopropylsulfonyl)-1,2,3,4-tetrahydroisoquinolin-7-yl]amino}pyrimidine-5-carboxamide | 61 |
| 2-{[(1R*,2S*)-2-aminocyclohexyl]amino}-4-{[2-(4-fluorobenzoyl)-1,2,3,4-tetrahydroisoquinolin-7-yl]amino}pyrimidine-5-carboxamide | 62 |
| 2-{[(1R*,2S*)-2-aminocyclohexyl]amino}-4-({1-[4-(methylthio)benzyl-1H-indol-4-yl}amino)pyrimidine-5-carboxamide | 63 |
| 2-{[(1R*,2S*)-2-aminocyclohexyl]amino}-4-[(2-pyridin-2-yl-1,2,3,4-tetrahydroisoquinolin-7-yl)amino]pyrimidine-5-carboxamide | 64 |
| 2-{[(1R*,2S*)-2-aminocyclohexyl]amino}-4-{[1-(2-methylbenzyl)-(1H-indol-4-yl]amino}pyrimidine-5-carboxamide | 65 |
| 5-{[(1R*,2S*)-2-aminocyclohexyl]amino}-7-[(3'-methylbiphenyl-3-yl)amino]imidazo[1,2-c]pyrimidine-8-carboxamide | 66 |
| 2-{[(1R*,2S*)-2-aminocyclohexyl]amino}-4-{[2-(3-methoxybenzoyl)-1,2,3,4-tetrahydroisoquinolin-7-yl]amino}pyrimidine-5-carboxamide | 67 |
| 2-{[(1R*,2S*)-2-aminocyclohexyl]amino}-4-{[2-(3-ethylbenzoyl)-1,2,3,4-tetrahydroisoquinolin-7-yl]amino}pyrimidine-5-carboxamide | 68 |
| 2-{[(1R*,2S*)-2-aminocyclohexyl]amino}-4-{[2-(cyclohexylcarbonyl)-1,2,3,4-tetrahydroisoquinolin-7-yl]amino}pyrimidine-5-carboxamide | 69 |
| 2-{[(1R*,2S*)-2-aminocyclohexyl]amino}-4-{[2-(isopropylsulfonyl)-1,2,3,4-tetrahydroisoquinolin-7-yl]amino}pyrimidine-5-carboxamide | 70 |
| 2-{[(1R*,2S*)-2-aminocyclohexyl]amino}-4-{[2-(2-methoxybenzoyl)-1,2,3,4-tetrahydroisoquinolin-7-yl]amino}pyrimidine-5-carboxamide | 71 |
| 2-{[(1R*,2S*)-2-aminocyclohexyl]amino}-4-{[2-(4-methylbenzoyl)-1,2,3,4-tetrahydroisoquinolin-7-yl]amino}pyrimidine-5-carboxamide | 72 |
| 2-{[(1R*,2S*)-2-aminocyclohexyl]amino}-4-{[2-(2-chlorobenzoyl)-1,2,3,4-tetrahydroisoquinolin-7-yl]amino}pyrimidine-5-carboxamide | 73 |
| 2-{[(1R*,2S*)-2-aminocyclohexyl]amino}-4-{[1-(2-chlorobenzyl)-(1H-indol-4-yl]amino}pyrimidine-5-carboxamide | 74 |
| 2-{[(1R*,2S*)-2-aminocyclohexyl]amino}-4-{[2-(2-fluorobenzoyl)-1,2,3,4-tetrahydroisoquinolin-7-yl]amino}pyrimidine-5-carboxamide | 75 |
| 2-{[(1R*,2S*)-2-aminocyclohexyl]amino}-4-{[3-(phenoxymethyl)phenyl]amino}pyrimidine-5-carboxamide | 76 |
| 2-{[(1R*,2S*)-2-aminocyclohexyl]amino}-4-{[2-(4-chlorobenzoyl)-1,2,3,4-tetrahydroisoquinolin-7-yl]amino}pyrimidine-5-carboxamide | 77 |
| 2-{[(1R*,2S*)-2-aminocyclohexyl]amino}-4-{[2-(cyclopentylcarbonyl)-1,2,3,4-tetrahydroisoquinolin-7-yl]amino}pyrimidine-5-carboxamide | 78 |
| 2-{[(1R*,2S*)-2-aminocyclohexyl]amino}-4-{[1-(3-chlorobenzyl)-(1H-indol-4-yl]amino}pyrimidine-5-carboxamide | 79 |
| 2-{[(1R*,2S*)-2-aminocyclohexyl]amino}-4-{[2-(3-methylbenzoyl)-1,2,3,4-tetrahydroisoquinolin-7-yl]amino}pyrimidine-5-carboxamide | 80 |
| 2-{[(1R*,2S*)-2-aminocyclohexyl]amino}-4-{[2-(cyclopropylcarbonyl)-1,2,3,4-tetrahydroisoquinolin-7-yl]amino}pyrimidine-5-carboxamide | 81 |
| 2-{[(1R*,2S*)-2-aminocyclohexyl]amino}-4-({2-[4-(methylthio)benzoyl]-1,2,3,4-tetrahydroisoquinolin-7-yl}amino)pyrimidine-5-carboxamide | 82 |
| 2-{[(1R*,2S*)-2-aminocyclohexyl]amino}-4-({2-(4-ethylbenzoyl)-1,2,3,4-tetrahydroisoquinolin-7-yl]amino}pyrimidine-5-carboxamide | 83 |
| 2-{[(1R*,2S*)-2-aminocyclohexyl]amino}-4-{[1-(3-methoxybenzyl)-(1H-indol-6-yl]amino}pyrimidine-5-carboxamide | 84 |
| 2-{[(1R*,2S*)-2-aminocyclohexyl]amino}-4-{[1-(4-methoxybenzyl)-(1H-indol-6-yl]amino}pyrimidine-5-carboxamide | 85 |
| 2-{[(1R*,2S*)-2-aminocyclohexyl]amino}-4-{[3-(4-methoxybenzyl)phenyl]amino}pyrimidine-5-carboxamide | 86 |
| 2-{[(1R*,2S*)-2-aminocyclohexyl]amino}-4-{[1-(2-methoxybenzyl)-(1H-indol-6-yl]amino}pyrimidine-5-carboxamide | 87 |
| 2-{[(1R*,2S*)-2-aminocyclohexyl]amino}-4-{[2-(2-ethylbenzoyl)-1,2,3,4-tetrahydroisoquinolin-7-yl]amino}pyrimidine-5-carboxamide | 88 |
| 2-{[(1R*,2S*)-2-aminocyclohexyl]amino}-4-{[2-(3-chlorobenzoyl)-1,2,3,4-tetrahydroisoquinolin-7-yl]amino}pyrimidine-5-carboxamide | 89 |

| NAME | Example number |
|---|---|
| 2-{[(1R*,2S*)-2-aminocyclohexyl]amino}-4-{[2-(pyridin-2-ylcarbonyl)-1,2,3,4-tetrahydroisoquinolin-7-yl]amino}pyrimidine-5-carboxamide | 90 |
| 2-{[(1R*,2S*)-2-aminocyclohexyl]amino}-4-{[1-(3-phenoxybenzyl)-(1H-indol-4-yl]amino}pyrimidine-5-carboxamide | 91 |
| 2-{[(1R*,2S*)-2-aminocyclohexyl]amino}-4-{[2-(4-methoxybenzoyl)-1,2,3,4-tetrahydroisoquinolin-7-yl]amino}pyrimidine-5-carboxamide | 92 |
| 2-{[(1R*,2S*)-2-aminocyclohexyl]amino}-4-[(3-methylphenyl)amino]pyrido[4,3-d]pyrimidin-5(6H)-one | 93 |
| 2-{[(1R*,2S*)-2-aminocyclohexyl]amino}-4-({2-[2-(methylthio)benzoyl]-1,2,3,4-tetrahydroisoquinolin-7-yl}amino)pyrimidine-5-carboxamide | 94 |
| 2-{[(1R*,2S*)-2-aminocyclohexyl]amino}-4-{[3-(4-chlorobenzyl)phenyl]amino}pyrimidine-5-carboxamide | 95 |
| 2-{[(1R*,2S*)-2-aminocyclohexyl]amino}-4-{[1-(biphenyl-4-ylmethyl)-1H-indol-4-yl]amino}pyrimidine-5-carboxamide | 96 |
| 2-{[(1R*,2S*)-2-aminocyclohexyl]amino}-4-[(2-benzyl-1,2,3,4-tetrahydroisoquinolin-7-yl)amino]pyrimidine-5-carboxamide | 97 |
| 2-{[(1R*,2S*)-2-aminocyclohexyl]amino}-4-({3-[(3-hydroxyphenyl)thio]phenyl}amino)pyrimidine-5-carboxamide | 98 |
| 2-{[(1R*,2S*)-2-aminocyclohexyl]amino}-4-({3-[(4-hydroxyphenyl)thio]phenyl}amino)pyrimidine-5-carboxamide | 99 |
| 2-{[(1R*,2S*)-2-aminocyclohexyl]amino}-4-({3-[(4-methoxyphenyl)thio]phenyl}amino)pyrimidine-5-carboxamide | 100 |
| 2-{[(1R*,2S*)-2-aminocyclohexyl]amino}-4-{[2-(2-methylbenzoyl)-1,2,3,4-tetrahydroisoquinolin-7-yl]amino}pyrimidine-5-carboxamide | 101 |
| 2-{[(1R*,2S*)-2-aminocyclohexyl]amino}-4-{[1-(4-hydroxybenzyl)-(1H-indol-6-yl]amino}pyrimidine-5-carboxamide | 102 |
| 2-{[(1R*,2S*)-2-aminocyclohexyl]amino}-4-{[3-(3-methylbenzyl)phenyl]amino}pyrimidine-5-carboxamide | 103 |
| 2-{[(1R,2S)-2-aminocyclohexyl]amino}-4-({3-[2-(methylamino)-2-oxoethoxy]phenyl}amino)pyrimidine-5-carboxamide | 104 |
| 2-{[(1R*,2S*)-2-aminocyclohexyl]amino}-4-{[1-(cyclopropylcarbonyl)-1,2,3,4-tetrahydroquinolin-7-yl]amino}pyrimidine-5-carboxamide | 105 |
| 2-{[(1R*,2S*)-2-aminocyclohexyl]amino}-4-({3-[(4-chlorophenyl)thio]phenyl}amino)pyrimidine-5-carboxamide | 106 |
| 5-{[(1R*,2S*)-2-aminocyclohexyl]amino}-7-[(2-methoxy-3'-methylbiphenyl-4-yl)amino]imidazo[1,2-c]pyrimidine-8-carboxamide | 107 |
| 2-{[(1R,2S)-2-aminocyclohexyl]amino}-4-{[1-(4-hydroxybenzyl)-1H-indol-4-yl]amino}pyrimidine-5-carboxamide | 108 |
| 2-{[(1R*,2S*)-2-aminocyclohexyl]amino}-4-{[2-(phenylsulfonyl)-1,2,3,4-tetrahydroisoquinolin-7-yl]amino}pyrimidine-5-carboxamide | 109 |
| 2-{[(1R*,2S*)-2-aminocyclohexyl]amino}-4-[(2-methyl-1,2,3,4-tetrahydroisoquinolin-7-yl)amino]pyrimidine-5-carboxamide | 110 |
| 2-{[(1R*,2S*R)-2-aminocyclohexyl]amino}-4-({3-[(3-methylphenyl)thio]phenyl}amino)pyrimidine-5-carboxamide | 111 |
| 2-{[(1R*,2S*)-2-aminocyclohexyl]amino}-4-{[1-(2-methoxybenzyl)-(1H-indol-5-yl]amino}pyrimidine-5-carboxamide | 112 |
| 2-{[(1R*,2S*)-2-aminocyclohexyl]amino}-4-({3-[(3-methoxyphenyl)thio]phenyl}amino)pyrimidine-5-carboxamide | 113 |
| 2-{[(1R*,2S*)-2-aminocyclohexyl]amino}-4-[(3-benzylphenyl)amino]pyrimidine-5-carboxamide | 114 |
| 2-{[(1R,2S)-2-aminocyclohexyl]amino}-4-[(3'-hydroxybiphenyl-3-yl)amino]-6-methylpyrimidine-5-carboxamide | 115 |
| 2-{[(1R*,2S*)-2-aminocyclohexyl]amino}-4-{[3-(phenylthio)phenyl]amino}pyrimidine-5-carboxamide | 116 |
| 2-{[(1R*,2S*)-2-aminocyclohexyl]amino}-4-[(4-benzylphenyl)amino]pyrimidine-5-carboxamide | 117 |
| 2-{[(1R*,2S*)-2-aminocyclohexyl]amino}-4-(1,2,3,4-tetrahydroisoquinolin-7-ylamino)pyrimidine-5-carboxamide | 118 |
| 2-{[(1R*,2S*)-2-aminocyclohexyl]amino}-4-{[4-(phenylthio)phenyl]amino}pyrimidine-5-carboxamide | 119 |
| 2-{[(1R,2S)-2-aminocyclohexyl]amino}-4-[(4'-hydroxybiphenyl-3-yl)amino]-6-methylpyrimidine-5-carboxamide | 120 |
| 2-{[(1R*,2S*)-2-aminocyclohexyl]amino}-4-[(2-isobutyryl-1,2,3,4-tetrahydroisoquinolin-7-yl)amino]pyrimidine-5-carboxamide | 121 |
| 2-{[(1R*,2S*)-2-aminocyclohexyl]amino}-4-{[1-(cyclopropylcarbonyl)-1,2,3,4-tetrahydroquinolin-5-yl]amino}pyrimidine-5-carboxamide | 122 |
| 2-{[(1R*,2S*)-2-aminocyclohexyl]amino}-4-{[1-(2-phenoxybenzyl)-(1H-indol-4-yl]amino}pyrimidine-5-carboxamide | 123 |

The following detailed experimental procedures show in detail how Examples 1, 2 and 4 may be prepared. Other Examples and other compounds of formula (Ia), (Ib) or (Ic) may be prepared by analogy using the common general knowledge of one skilled in the art (see, for example, Comprehensive Organic Chemistry, Ed. Barton and Ollis, Elsevier; Comprehensive Organic Transformations: A Guide to Functional Group Preparations, Larock, John Wiley and Sons).

HPLC methods A, B and C referred to below are as follows:

| Method A | | |
|---|---|---|
| HPLC conditions | Analytical (QC) | Preparative |
| Column | Gemini-NX 3 μm C18 110A | Gemini-NX 5 μm C18 21.2 × 100 mm |
| Temperature | Ambient | Ambient |
| Detection | UV 225 nm-ELSD-MS | UV 225 nm-ELSD-MS |
| Injection volume | 5 μL | 1000 μL |
| Flow rate | 1.5 mL/min | 18 mL/min |
| Mobile phase | A: H2O + 0.1% ammonium acetate B: MeCN + 0.1% ammonium acetate | A: H2O + 0.1% DEA B: MeCN + 0.1% DEA |

| Gradient | Time (min) | % B | Time (min) | % B |
|---|---|---|---|---|
| | 0 | 5 | 0-1.0 | 5 |
| | 0-3.0 | 5-95 | 1.0-7.0 | 5-98 |
| | 3.0-4.0 | 95 | 7.0-9.0 | 98 |
| | 4.0-4.1 | 95-5 | 9.0-9.10 | 98-5 |
| | 4.1-5.0 | 5 | 9.10-10 | 5 |

| Method B | | |
|---|---|---|
| HPLC conditions | Analytical (QC) | Preparative |
| Column | Gemini-NX 3 μm C18 110A | Gemini-NX 5 μm C18 21.1 × 100 mm |
| Temperature | Ambient | Ambient |
| Detection | UV 225 nm-ELSD-MS | UV 225 nm-ELSD-MS |
| Injection volume | 5 μL | 1000 μL |

Method B

| | Time (min) | % B | Time (min) | % B |
|---|---|---|---|---|
| Flow rate | 1.5 mL/min | | 18 mL/min | |
| Mobile phase | A: H2O + 0.1% formic | | A: H2O + 0.1% formic | |
| | B: MeCN + 0.1% formic acid | | B: MeCN + 0.1% formic acid | |
| Gradient | 0 | 5 | initial | 20 |
| | 0-3.0 | 5-95 | 1 | 20 |
| | 3.0-4.0 | 95 | 5.4 | 70 |
| | 4.0-4.1 | 95-5 | 6.33 | 98 |
| | 4.1-5.0 | 5 | 6.4 | 20 |
| | | | 7 | 20 |

Method C

| HPLC conditions | Preparative |
|---|---|
| Column | Phenomenex Luna C18 5 μm-100 Å 21.2 × 150 mm |
| Temperature | Ambient |
| Detection | UV 254 nm-ELSD-MS |
| Injection volume | 1000 μL |
| Flow rate | 18 mL/min |
| Mobile phase | A: H2O + 0.05% formic acid B: MeCN + 0.05% formic acid |

| Gradient | Time (min) | % B |
|---|---|---|
| | 0-2.5 | 5 |
| | 2.5-17.5 | 5-95 |
| | 17.5-22.5 | 95 |
| | 22.5-22.6 | 95-5 |
| | 22.6-23.0 | 5 |

Example 1

2-{[(1R*,2S*)-2-Aminocyclohexyl]amino}-4-(1H-indol-4-ylamino)pyrido[4,3-d]pyrimidin-5(6H)-one

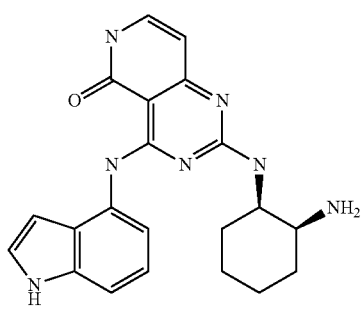 [SMILES: N[C@H]1CCCC[C@H]1Nc1nc(Nc2cccc3[nH]ccc23)c2c(=O)[nH]ccc2n1]

Step (1): 4-(1H-Indol-4-ylamino)-6-methyl-2-methylsulfanyl-pyrimidine-5-carboxylic acid ethyl ester

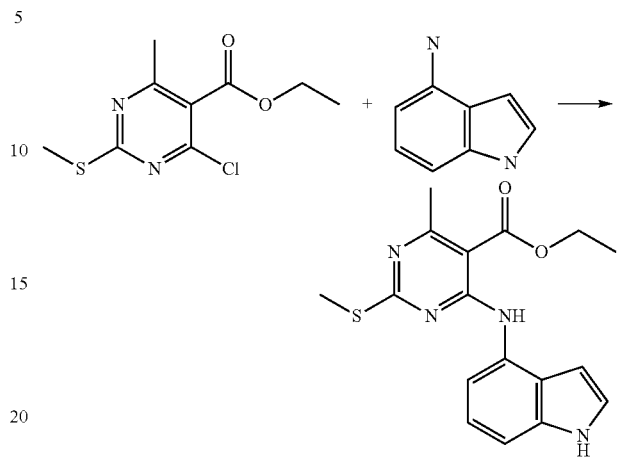

The chloropyrimidine and amino indole (both commercially available) were combined in DMF and heated at 70° C. overnight. LCMS showed a major peak (89% by ELSD @ 1.38 min) for product mass ion (ES+343). DMF removed in vacuo to give an orange solid. Slurried in hot TBME/water and cooled to room temperature. Filtered off to give the product as a grey solid. LCMS: m/z 343 MH+.

Step (2) 4-(1H-Indol-4-ylamino)-6-methyl-2-methylsulfanyl-pyrimidine-5-carboxylic acid

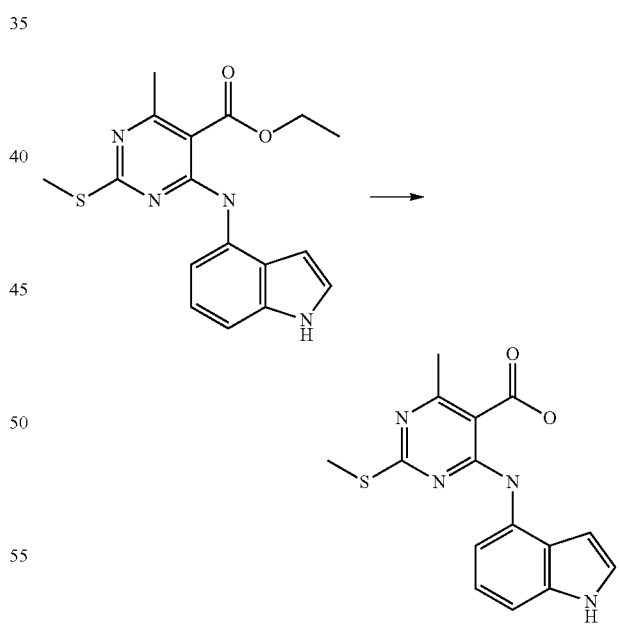

To a solution of the ester from Step (1) (3.5 g) in EtOH (30 ml) was added aqueous NaOH (1M, 20 ml). Reaction mixture stirred at 70° C. for 2 hours. LCMS showed complete conversion to a major new product with mass ion consistent for desired product. Reaction mixture cooled to room temperature and EtOH removed in vacuo to give a solid. 20 ml water added and acidified to pH 4/5 with 2N HCl. A green solid formed and was filtered off. The resulting paste was washed with diethyl ether, dried under high vacuum, at 65° C. for 2 hours to give the desired product as a green solid.

LCMS: m/z 315 MH+.

Step (3): 4-(1H-Indol-4-ylamino)-6-methyl-2-methylsulfanyl-pyrimidine-5-carboxylic acid amide

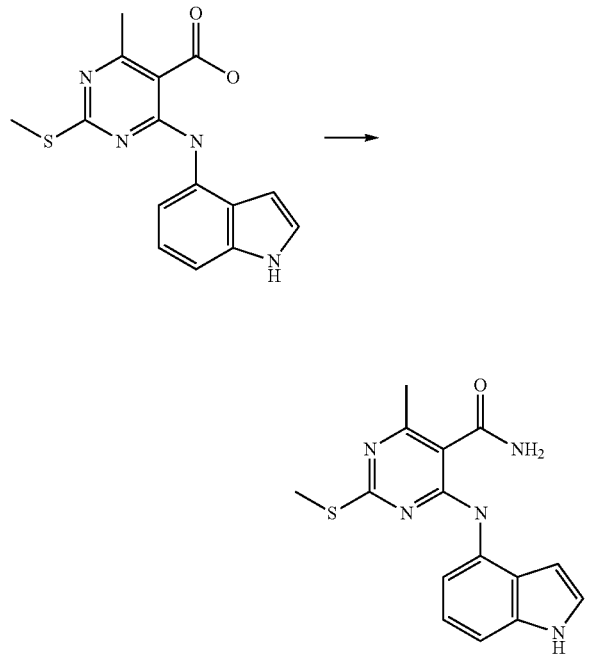

Acid from Step (2) taken up in DMF, to which was added HOBt and EDC.HCl. After stirring at room temperature for 40 minutes, ammonia was added and the reaction mixture stirred at room temperature overnight. LCMS showed ~50% SM: product. Reaction mixture evaporated down and re-subjected to more reagents. After 2 hours reaction now shows full conversion to desired product. Reaction mixture evaporated. Residue taken up in EtOAc/water, remaining precipitate filtered and washed with water/EtOAc and dried under vacuo to give a green solid.

LCMS: m/z ES+314 (MH+).

Preparation 4: 4-(1H-Indol-4-ylamino)-2-methylsulfanyl-6H-pyrido[4,3-d]pyrimidin-5-one

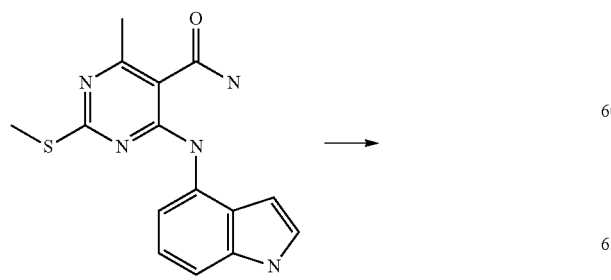

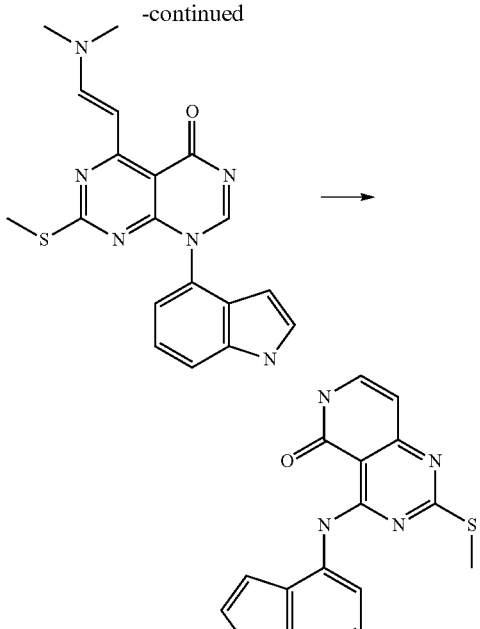

Pyrimidine from Step (3) dissolved in DMF, DMF-DMA added and stirred together at 85° C. for 1 hour. Reaction mixture cooled after this time and evaporated in vacuo, solvent reduced to almost dryness, to give a dark brown residue/oil. Residue stirred in glacial AcOH (1 ml) at reflux (110° C.) for 4 hours then cooled to room temperature overnight. Reaction mixture evaporated to give dark brown residue which was dry-loaded on a silica column. Eluted with 99:1:0.1 to 90:10:1 (DCM: MeOH: ammonia) and product fractions collected to give a yellow solid.

LCMS: m/z 324, MH+.

Step (5): 4-(1H-Indol-4-ylamino)-2-methanesulfinyl-6H-pyrido[4,3-d]pyrimidin-5-one

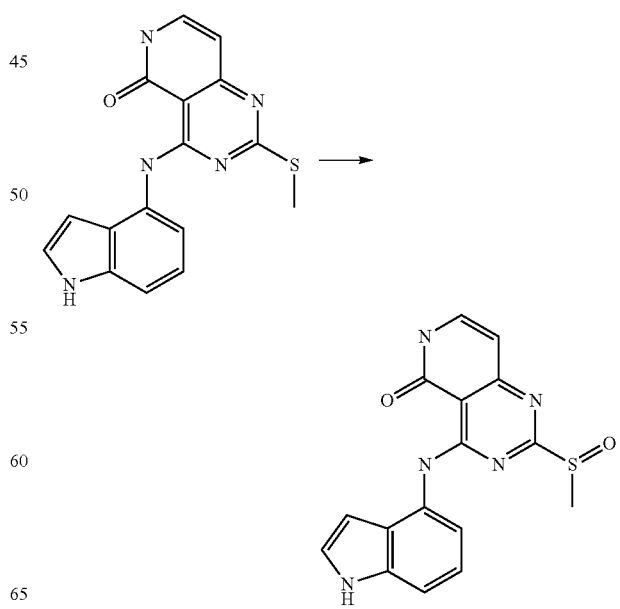

m-CPBA (45 mg, 0.2 mmol) was added portionwise to a solution of sulfide from Step (4) (26 mg, 0.08 mmol) in DMF (0.4 mL) at 0° C. Mixture stirred for 10 mins at 0° C. and then allowed to warm to room temperature overnight. A further 1 eq m-CPBA was added and the reaction mixture was allowed to warm to room temperature. After a further 3 hours the product was filtered off, washing with minimal DCM to give a yellow solid.

LCMS: m/z 340 (MH$^+$).

Step (6): Final Product

Sulfoxide from Step (5) (14 mg, 0.04 mmol) and 25 mg cis-1,2-cyclohexanediamine (5 eq) combined in 1 mL DMSO and stirred together at 100° C. overnight. Purified by preparative HPLC (Method A).

LCMS m/z+390 (MH+).

Example 2

2-{[1R*,2S*)-2-Aminocyclohexyl]amino}-4-({1-[3-(4-hydroxyphenyl)propyl]-1H-indol-4-yl}amino)pyrimidine-5-carboxamide Step (1); 1-[3-(4-Methoxyphenyl)propyl]-1H,4-aminoindole Nitro-indole (100 mg, 0.617 mmol), phosphine (279 mg, 0.925 mmol) and alcohol (0.617 mmol) were heated at 80° C. in toluene (2 mL) overnight. The mixture was cooled down to room temperature. To the mixture was added 10% Pd/C (10 mg) and ammonium acetate (389 mg, 6.17 mmol). The mixture was stirred at 60° C. for 2 hours then filtered on arbocel under nitrogen. The arbocel pad was washed with EtOH. The mixture was evaporated in vacuo. The residue was dissolved in MeOH and passed through an SCX-2 cartridge. The cartridge was washed with MeOH (25 mL). The cartridge was then flushed with a 2M methanolic ammonia solution (25 mL). The ammonia solution was evaporated to afford the product as a red oil LCMS m/z 281 MH+

Step (2): 2-Chloro-4-{1-[3-(4-methoxy-phenyl)-propyl]-1H-indol-4-ylamino}-pyrimidine-5-carboxylic acid

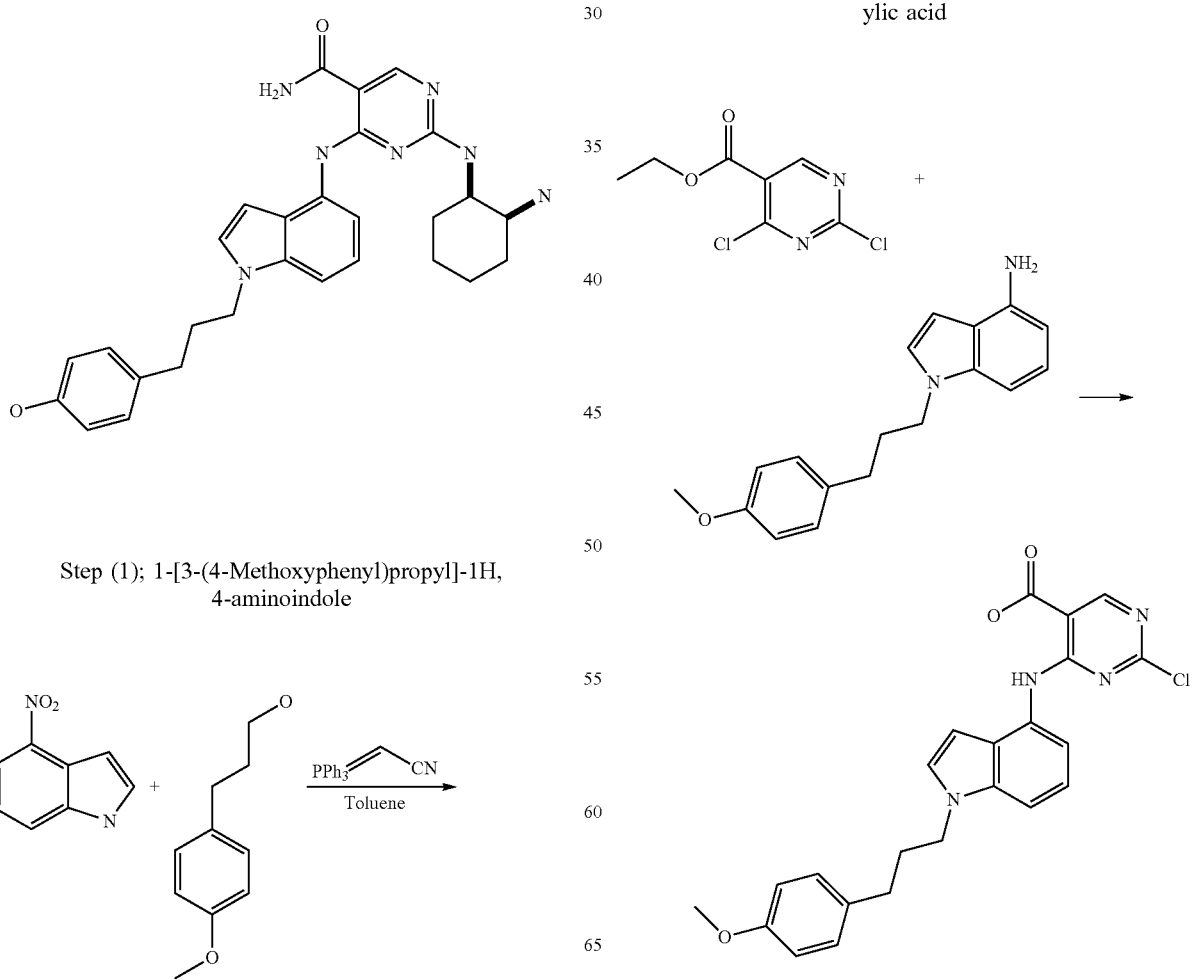

To a solution of the dichloropyrimidine (93.5 mg, 0.423 mmol) in dry THF (2 mL) at −78° C. was added dropwise a solution of the aminoindole from Step (1) (119 mg, 0.423 mmol) in dry THF (2 mL) followed by DIPEA (81 uL, 0.465 mmol). The mixture was warmed to room temperature overnight. Water (20 mL) was added to the mixture. The mixture was extracted twice with EtOAc (10 mL). The EtOAc layers were combined, washed with brine and dried through a phase separating cartridge. The residue was dissolved in THF (2 mL) and a 1 M aqueous sodium hydroxide solution (0.592 mL, 0.592 mmol) was added. The mixture was stirred at room temperature overnight. The mixture was treated with a 1 M solution of hydrochloric acid (600 uL). The mixture was filtered and washed with water. The solid was dried in vacuo at 45° C. overnight.

LCMS: m/z 437 $M^{35}ClH^+$.

Step (3): 2-((1R*,2*)-2-Amino-cyclohexylamino)-4-{1-[3-(4-methoxy-phenyl)-propyl]-1H-indol-4-ylamino}-pyrimidine-5-carboxylic acid amide

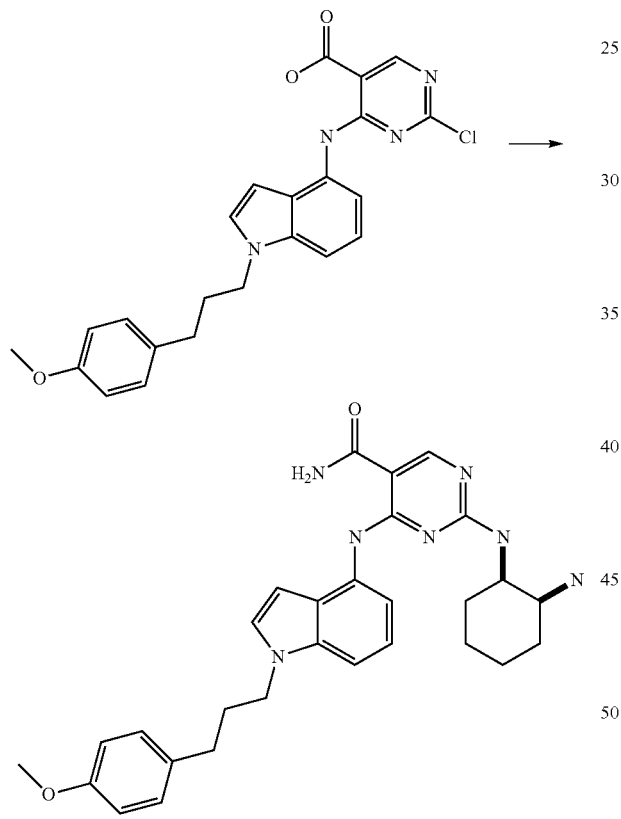

To the acid from Step (2) (0.23 mmol) in DMF (2 mL) was added EDC.Cl (53 mg, 0.275 mmol) and HOBt (42 mg, 0.275 mmol). The mixture was stirred at room temperature for 1 hour. 0.88 Ammonia (71 uL, 3.66 mmol) was added dropwise to the mixture. The mixture was stirred at room temperature for 2 hours. LCMS showed completion of the reaction. The mixture was treated with a saturated aqueous $K_2CO_3$ solution (10 mL). The mixture was extracted twice with EtOAc (5 mL). The organic layers were combined, dried through a phase separating cartridge and evaporated in vacuo. The residue was dissolved in THF (2 mL). The mixture was treated with cis 1,2-cyclohexanediamine (40 uL, 0.343 mmol) followed by DIPEA (48 uL, 0.275 mmol). The mixture was stirred at 60° C. overnight. The precipitate was filtered, washed with THF and dried under vacuum at 45° C. overnight.

LCMS: m/z 514 $MH^+$.

Step (4): Final Product

The anisole from Step (3) (62 mg, 0.12 mmol) in DCM (500 uL) was treated with a 1M $BBr_3$ in solution in DCM (1.20 mL, 1.20 mmol). The mixture was stirred at room temperature for 3 hours. The mixture was treated with aqueous ammonia (880) (2 mL). The mixture was stirred at room temperature for 1 hour. The mixture was filtered. The resulting gum was dissolved in MeOH. The MeOH solution was evaporated in vacuo. The residue was purified by preparative HPLC (Method A).

LCMS: m/z 500 $MH^+$.

Example 4

2-{[(1R*,2S*)-2-Aminocyclohexyl]amino}-4-[(4'-hydroxybiphenyl-3-yl)amino]pyrimidine-5-carboxamide Step (1): 4-(3-Iodo-phenylamino)-2-methylsulfanyl-pyrimidine-5-carboxylic acid

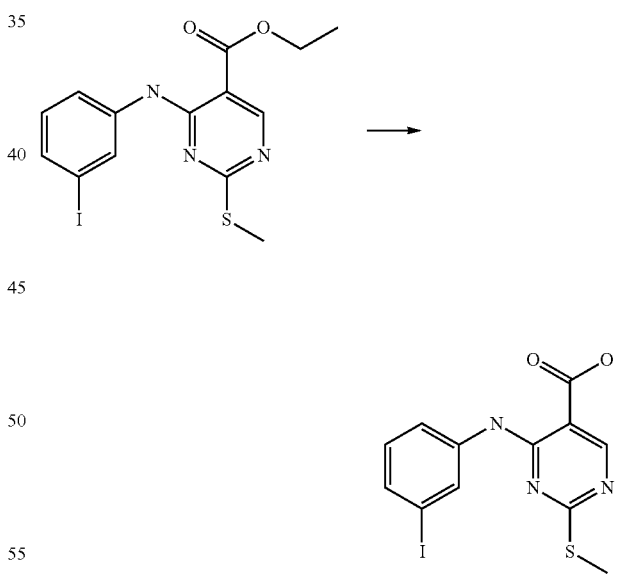

Aryl iodide (prepared as in WO-2009/136995) was treated with 1M NaOH and THF. Slight yellow colour developed on addition of the hydroxide followed by rapid precipitation. Mixture heated at 50° C. for 2 hours, after which time the precipitate had dissolved and LCMS showed complete reaction. 2M HCl (10 ml) was added to neutralise and the resulting solid was collected by filtration, to yield a white solid.

LCMS: m/z 388 $MH^+$, 386 $(M-H)^-$.

Step (2): 4-(3-Iodo-phenylamino)-2-methylsulfanyl-pyrimidine-5-carboxylic acid amide

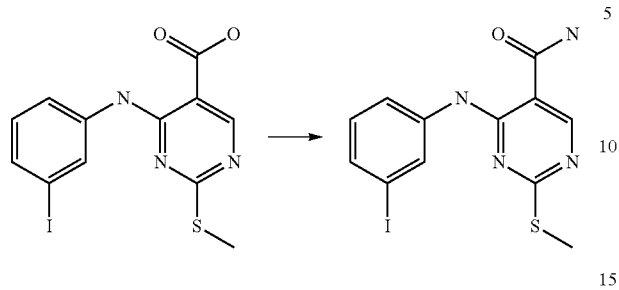

Acid from Step (1) taken up in DMF, to which was added HOBt and EDC.HCl. After stirring at room temperature for 40 minutes, ammonia was added and the reaction stirred at room temperature overnight (heavy precipitation occurred on addition of ammonia).

Precipitate collected by filtration to yield a white solid 4.13 g.

LCMS m/z 387 MH$^+$, 385 (M-H).

Step (3): 4-(3-Iodo-phenylamino)-2-methylsulfonyl-pyrimidine-5-carboxylic acid amide

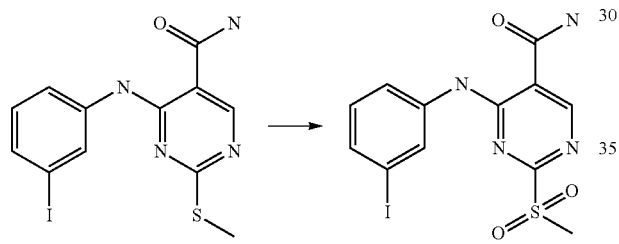

m-CPBA was added portionwise to a solution of sulfide from Step (2) in DMF at 0° C. Mixture stirred for 10 mins at 0° C. and then allowed to warm to room temperature overnight. Some solid had precipitated, so this was collected by filtration, 1.11 g. Methanol was added to the filtrate, which caused further precipitate to form. This was also collected by filtration, 1.5 g. On standing the filtrate began to precipitate further, so one final crop was collected by filtration, 520 mg. Combined total yield 3.13 g.

LCMS: m/z 419 MH$^+$, 417 (M-H).

Step (4): {(1R*,2S*)-2-[5-Carbamoyl-4-(3-iodo-phenylamino)-pyrimidin-2-ylamino]-cyclohexyl}-carbamic acid tert-butyl ester

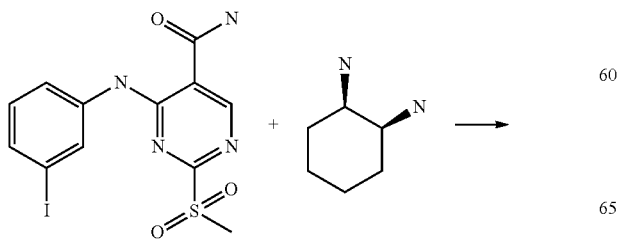

-continued

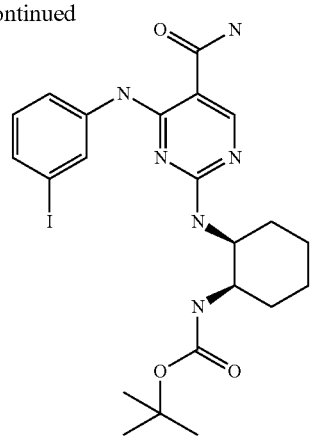

Sulfone from Step (3) and cis-1,2-cyclohexanediamine were combined in DMSO and heated at 80° C. overnight. Partitioned between EtOAc and water (100 ml each). Organics washed with water (50 ml) and brine (50 ml), dried over MgSO$_4$ and concentrated to yield an orange oil, still heavily contaminated with DMF. Residue taken up in DCM, to which was added Boc$_2$O. Reaction stirred at room temperature overnight. Solvent evaporated.

Purification by ISCO Redisep 80 g, eluting with heptane: EtOAc, 100:0 to 0:100 to yield the desired compound as a cream solid.

LCMS: m/z 553 MH$^+$.

Step 5: Final Product

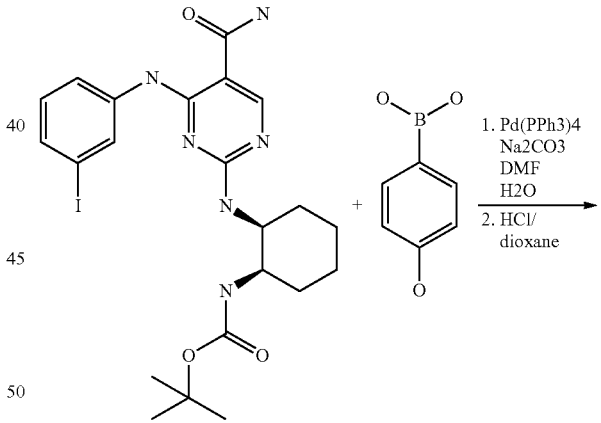

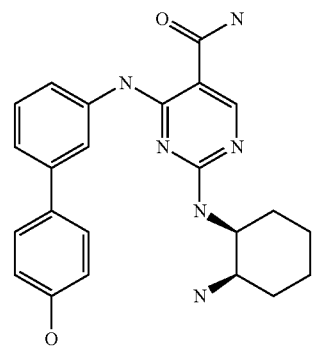

Iodide from Step (4), boronic acid and sodium carbonate combined in DMF. Mixture degassed with nitrogen.

Pd(PPh3)4 (5 mol %) added and reaction heated to 60° C. over the weekend. LCMS shows complete reaction. Reaction concentrated to low volume and residue treated with 4M HCl in dioxane. Stirred at room temperature for 1.5 hours, after which time the Boc removal was complete. Solvent evaporated. Residue was purified by preparative HPLC (Method A)

LCMS: m/z 419 MH$^+$, 417 (M-H)$^-$.

The activity of the compounds of formula (Ia), (Ib) or (Ic) may be assessed in the following assay.

Syk Enzyme Activity

The Promega ADP-Glo Kinase Assay is a luminescent ADP detection assay that provides a universal, homogeneous, high-throughput screening method to measure kinase activity by quantifying the amount of ADP produced during a kinase reaction. (See FIG. 1.)

Assay Buffer:

| Stock ingredients | Vol/Mass | Concentration in Buffer | Supplier and ref |
|---|---|---|---|
| 1M Tris | | 25 mM (2.5 ml in 100 ml) | Sigma T2663 |
| 1% Tween 20 | | 0.01% (1 ml in 100 ml) | Sigma P2443 |
| 1M MgCl2 | | 10 mM (1 ml in 100 ml) | Sigma M1028 |
| 1M DDT | | 1 mM (10 ul/10 ml) | Sigma 646563 |
| Water | | | |

Note 1:
Assay buffer (minus DDT) stable at room temp for at least a week
Note 2:
DDT always added fresh on the day of the experiment Compound Diluent

| Stock ingredients | Vol/Mass | Concentration in Buffer | Supplier and ref |
|---|---|---|---|
| 5% Pluronic (F127) in dH20 | | 0.05% (1 ml in 100 ml) | Sigma P2443 |
| 95% Water | | | |

Enzyme Preparation

| Ingredients | Vol/Mass | Concentration in Working Solution | Supplier and ref |
|---|---|---|---|
| SYK Enzyme (1.9 uM) 100% DMSO | | 3.75 nM (1.5 nM FAC) | Invitrogen PV089 Lot # 716672D 0.19 mg/ml |

ATP & Peptide Preparation

| Ingredients | Vol/Mass | Concentration in Working Solution | Supplier and ref |
|---|---|---|---|
| Peptide 9 (1.5 mM) 100% DMSO | | 5 uM (2 uM FAC) | Anaspec 64141 Lot # 72634 Add 455 ul DMSO to 1 mg vial |
| ATP (10 mM) | | 100 uM (40 uM FAC) | From ADP-Glo Kit |

Peptide diluted 1:300 in assay buffer
ATP diluted 1:100 in assay buffer
Note:
Aliquots stored at −20

ADP-Glo Kit
Promega V9102, prepared as kit instructions.
http://www.promega.com/tbs/tm313/tm313.pdf Method Spin compound plates (0.4 ul in 100% DMSO) at 100 rpm for 1 min Add 30 ul of compound diluent per well to compound plate=52.6 uM Transfer 2 ul/well to low volume assay plate.

1 Add enzyme to plate
4 ul/well Run enzyme onto a dummy plate, prior to addition of enzyme to compound plate (coats tubing). Incubate at room temp for 15 mins.
2 Add Peptide/ATP mix to start reaction
4 ul/well Run ATP/peptide mix onto a dummy plate, prior to addition of ATP/peptide mix to compound plate (coats tubing). Incubate for 60 mins at room temperature.
3 At the end of the reaction time add ADP-Glo reagent
4 ul/well Incubate for 60 mins at room temp
4 Add ADP-Glo detection reagent
8 ul/well Incubate at room temp for 30 mins.
5 Read luminescence on either Analyst (Protocol 401) or Envision (Standard USM Luminescence) [ADP Glo (LF)]
2 ul Compound (5 fold dilution)
4 ul Enzyme (2.5 fold dilution)
4 ul Peptide/ATP mix (2.5 fold dilution)

The following Table shows the IC$_{50}$ data for Examples 1-123 in the assay described above.

| Example number | SYK IC$_{50}$ |
|---|---|
| 1 | 0.809 nM (0.000498-1310 n = 2) |
| 2 | 1.18 nM (0.0252-55.1 n = 2) |
| 3 | 1.37 nM (0.161-11.6 n = 3) |
| 4 | 1.57 nM (0.000230-10700 n = 2) |
| 5 | 2.50 nM (0.0542-115 n = 2) |
| 6 | 2.76 nM (0.900-8.45 n = 2) |
| 7 | 3.02 nM (0.0168-543 n = 2) |
| 8 | 3.27 nM (2.64-4.04 n = 4) |
| 9 | 3.40 nM (0.652-17.7 n = 2) |
| 10 | 3.63 nM (0.491-26.8 n = 2) |
| 11 | 3.86 nM |
| 12 | 4.15 nM (2.84-6.06 n = 2) |
| 13 | 4.47 nM (1.19-16.8 n = 2) |
| 14 | 4.75 nM (1.92-11.8 n = 2) |
| 15 | 4.96 nM (0.395-62.4 n = 2) |
| 16 | 4.97 nM (2.70-9.17 n = 4) |
| 17 | 5.48 nM (0.0278-1080 n = 2) |
| 18 | 5.49 nM (2.56-11.7 n = 2) |
| 19 | 5.62 nM (0.169-187 n = 2) |
| 20 | 5.67 nM (0.0806-399 n = 2) |
| 21 | 5.71 nM (0.135-242 n = 2) |
| 22 | 5.87 nM (0.382-90.3 n = 2) |
| 23 | 6.08 nM (0.824-44.9 n = 2) |
| 24 | 6.25 nM (5.48-7.12 n = 2) |
| 25 | 7.59 nM (0.178-325 n = 2) |
| 26 | 9.04 nM (4.00-20.5 n = 4) |
| 27 | 9.25 nM (0.146-588 n = 2) |
| 28 | 10.5 nM (0.222-496 n = 2) |
| 29 | 10.7 nM (0.427-269 n = 2) |
| 30 | 10.8 nM (0.309-377 n = 2) |
| 31 | 11.1 nM (3.42-35.8 n = 3) |
| 32 | 12.0 nM (3.51-41.1 n = 2) |
| 33 | 12.1 nM (0.149-979 n = 2) |
| 34 | 12.2 nM |
| 35 | 12.3 nM (6.45-23.6 n = 2) |
| 36 | 12.4 nM (1.85-83.6 n = 2) |
| 37 | 12.7 nM (1.84-87.2 n = 2) |
| 38 | 14.9 nM (9.69-22.8 n = 2) |
| 39 | 15.1 nM (0.000492-463000 n = 2) |
| 40 | 15.2 nM (1.25-184 n = 2) |
| 41 | 15.3 nM (0.209-1120 n = 2) |
| 42 | 15.4 nM (2.18-109 n = 2) |
| 43 | 15.9 nM (7.51-33.5 n = 2) |
| 44 | 16.6 nM (0.349-785 n = 2) |

| Example number | SYK IC$_{50}$ |
|---|---|
| 45 | 17.4 nM (11.3-26.9 n = 2) |
| 46 | 17.4 nM (4.48-67.9 n = 2) |
| 47 | 17.6 nM (6.64-46.4 n = 6) |
| 48 | 17.6 nM (2.99-103 n = 2) |
| 49 | 17.9 nM (13.5-23.8 n = 3) |
| 50 | 17.9 nM (3.30-97.8 n = 2) |
| 51 | 19.0 nM (0.000166–2.18E6 n = 2) |
| 52 | 21.0 nM (3.21-137 n = 2) |
| 53 | 21.4 nM (3.58-128 n = 2) |
| 54 | 21.5 nM (6.56-70.7 n = 2) |
| 55 | 22.2 nM (2.53-195 n = 2) |
| 56 | 23.8 nM (3.41-166 n = 2) |
| 57 | 24.0 nM (15.0-38.6 n = 3) |
| 58 | 24.2 nM (0.600-977 n = 2) |
| 59 | 24.3 nM (0.111-5310 n = 2) |
| 60 | 24.9 nM (0.00150-412000 n = 2) |
| 61 | 24.9 nM (4.29-145 n = 2) |
| 62 | 25.3 nM (1.87-342 n = 2) |
| 63 | 25.4 nM (23.7-27.2 n = 2) |
| 64 | 27.9 nM (18.1-42.8 n = 4) |
| 65 | 28.0 nM (27.3-28.8 n = 2) |
| 66 | 28.3 nM (0.200-4030 n = 2) |
| 67 | 28.8 nM (7.95-105 n = 3) |
| 68 | 29.4 nM (0.206-4200 n = 2) |
| 69 | 30.5 nM (5.07-183 n = 2) |
| 70 | 30.6 nM (5.98-156 n = 2) |
| 71 | 31.3 nM (8.28-118 n = 2) |
| 72 | 31.4 nM (0.985-999 n = 2) |
| 73 | 31.4 nM (0.273-3620 n = 2) |
| 74 | 32.2 nM (1.32-783 n = 2) |
| 75 | 33.6 nM (18.8-59.9 n = 2) |
| 76 | 33.7 nM (0.0119-94900 n = 2) |
| 77 | 34.8 nM (1.21-1000 n = 2) |
| 78 | 35.7 nM (1.82-700 n = 2) |
| 79 | 36.1 nM (20.8-62.6 n = 3) |
| 80 | 36.4 nM (9.22-144 n = 2) |
| 81 | 36.9 nM (9.88-138 n = 2) |
| 82 | 37.4 nM (0.302-4630 n = 2) |
| 83 | 40.6 nM (1.22-1360 n = 2) |
| 84 | 41.1 nM (21.1-80.2 n = 3) |
| 85 | 42.4 nM (23.8-75.8 n = 3) |
| 86 | 44.9 nM (0.0261-77100 n = 2) |
| 87 | 45.8 nM (35.5-59.1 n = 2) |
| 88 | 48.4 nM (27.3-85.7 n = 2) |
| 89 | 48.6 nM (0.990-2390 n = 2) |
| 90 | 48.9 nM (19.9-120 n = 2) |
| 91 | 55.1 nM (0.0972-31200 n = 2 |
| 92 | 56.0 nM (0.0169-186000 n = 2) |
| 93 | 60.9 nM (39.1-94.8 n = 4) |
| 94 | 61.3 nM (4.55-824 n = 2) |
| 95 | 69.9 nM (0.305-16000 n = 2) |
| 96 | 72.4 nM (12.2-431 n = 2) |
| 97 | 72.6 nM (29.5-179 n = 2) |
| 98 | 72.9 nM (7.46-713 n = 2) |
| 99 | 74.5 nM (40.2-138 n = 2) |
| 100 | 75.9 nM (0.00111-5.22E6 n = 2) |
| 101 | 78.4 nM (4.73-1300 n = 2) |
| 102 | 94.9 nM (2.00-4520 n = 2) |
| 103 | 96.3 nM (1.59-5830 n = 2) |
| 104 | 98.3 nM (95.2-101 n = 2) |
| 105 | 113 nM (3.51-3670 n = 2) |
| 106 | 118 nM (0.303-46400 |
| 107 | 130 nM (0.204-83200 n = 2) |
| 108 | 133 nM (77.0-230 n = 4) |
| 109 | 135 nM (0.0947-192000 n = 2) |
| 110 | 139 nM (43.1-449 n = 2) |
| 111 | 142 nM (46.8-431 n = 2) |
| 112 | 171 nM |
| 113 | 173 nM (73.8-405 n = 2) |
| 114 | 174 nM (79.3-381 n = 4) |
| 115 | 212 nM (6.20-7250 n = 2) |
| 116 | 215 nM (151-307 n = 4) |
| 117 | 225 nM (7.26-6960 n = 2) |
| 118 | 245 nM (19.9-3020 n = 2) |
| 119 | 267 nM (233-305 n = 2) |
| 120 | 272 nM (11.4-6510 n = 2) |
| 121 | 273 nM (5.27-14100 n = 2) |
| 122 | 284 nM (0.402-201000 n = 2) |
| 123 | 298 nM (127-701 n = 2) |

The invention claimed is:

1. A compound selected from the group consisting of:
2-{[(1R*,2S*)-2-aminocyclohexyl]amino}-4-({1-[3-(4-hydroxyphenyl)propyl]-1H-indol-4-yl}amino)pyrimidine-5-carboxamide;
2-{[(1R*,2S*)-2-aminocyclohexyl]amino}-4-({1-[3-(3-hydroxyphenyl)propyl]-1H-indol-4-yl}amino)pyrimidine-5-carboxamide;
2-{[(1R*,2S*)-2-aminocyclohexyl]amino}-4-[(4'-hydroxybiphenyl-3-yl)amino]pyrimidine-5-carboxamide;
2-{[(1R*,2S*)-2-aminocyclohexyl]amino}-4-[(3'-hydroxybiphenyl-3-yl)amino]pyrimidine-5-carboxamide;
2-{[(1R*,2S*)-2-aminocyclohexyl]amino}-4-{[1-(4-methylbenzyl)-1H-indol-4-yl]amino}pyrimidine-5-carboxamide;
2-{[(1R*,2S*)-2-aminocyclohexyl]amino}-4-({1-[3-(3-methoxyphenyl)propyl]-1H-indol-4-yl}amino)pyrimidine-5-carboxamide;
2-{[(1R,2S*)-2-aminocyclohexyl]amino}-4-[(3'-hydroxybiphenyl-3-yl)amino]pyrimidine-5-carboxamide;
2-{[(1R*,2S*)-2-aminocyclohexyl]amino}-4-{[1-(3-methylbenzyl)-1H-indol-4-yl]amino}pyrimidine-5-carboxamide;
2-{[(1R,2S)-2-aminocyclohexyl]amino}-4-[(1-benzyl-1H-indol-4-yl)amino]pyrimidine-5-carboxamide;
2-{[(1R*,2S*)-2-aminocyclohexyl]amino}-4-[(3,5-dimethoxyphenyl)amino]-6-hydroxypyrimidine-5-carboxamide;
2-{[(1R*,2S*)-2-aminocyclohexyl]amino}-4-{[2-(pyridin-3-ylcarbonyl)-1,2,3,4-tetrahydroisoquinolin-7-yl]amino}pyrimidine-5-carboxamide;
2-{[(1R,2S)-2-aminocyclohexyl]amino}-4-[(4'-hydroxybiphenyl-3-yl)amino]pyrimidine-5-carboxamide;
2-{[(1R*,2S*)-2-aminocyclohexyl]amino}-4-({1-[2-(4-hydroxyphenyl)ethyl]-1H-indol-4-yl}amino)pyrimidine-5-carboxamide;
2-{[(1R*,2S*)-2-aminocyclohexyl]amino}-4-{[2-(cyclobutylcarbonyl)-1,2,3,4-tetrahydroisoquinolin-7-yl]amino}pyrimidine-5-carboxamide;
2-{[(1R*,2S*)-2-aminocyclohexyl]amino}-4-{[2-(phenylacetyl)-1,2,3,4-tetrahydroisoquinolin-7-yl]amino}pyrimidine-5-carboxamide;
2-{[(1R*,2S*)-2-aminocyclohexyl]amino}-4-[(3'-methylbiphenyl-3-yl)amino]pyrimidine-5-carboxamide;
2-{[(1R*,2S*)-2-aminocyclohexyl]amino}-4-({1-[3-(4-methoxyphenyl)propyl]-1H-indol-4-yl}amino)pyrimidine-5-carboxamide;
2-{[(1R*,2S*)-2-aminocyclohexyl]amino}-4-[(2-propionyl-1,2,3,4-tetrahydroisoquinolin-7-yl)amino]pyrimidine-5-carboxamide;
2-{[(1R*,2S*)-2-aminocyclohexyl]amino}-4-({1-[2-(4-methoxyphenyl)ethyl]-1H-indol-4-yl}amino)pyrimidine-5-carboxamide;
2-{[(1R*,2S*)-2-aminocyclohexyl]amino}-4-{[1-(4-chlorobenzyl)-1H-indol-4-yl]amino}pyrimidine-5-carboxamide;

2-{[(1R*,2S*)-2-aminocyclohexyl]amino}-4-({1-[2-(3-hydroxyphenyl)ethyl]-1H-indol-4-yl}amino)pyrimidine-5-carboxamide;

2-{[(1R*,2S*)-2-aminocyclohexyl]amino}-4-({1-[3-(2-methoxyphenyl)propyl]-1H-indol-4-yl}amino)pyrimidine-5-carboxamide;

2-{[(1R*,2S*)-2-aminocyclohexyl]amino}-4-[(2-isonicotinoyl-1,2,3,4-tetrahydroisoquinolin-7-yl)amino]pyrimidine-5-carboxamide;

2-{[(1R*,2S*)-2-aminocyclohexyl]amino}-4-({1-[2-(2-hydroxyphenyl)ethyl]-1H-indol-4-yl}amino)pyrimidine-5-carboxamide;

2-{[(1R*,2S*)-2-aminocyclohexyl]amino}-4-{[2-(4-hydroxybenzoyl)-1,2,3,4-tetrahydroisoquinolin-7-yl]amino}pyrimidine-5-carboxamide;

2-{[(1R,2S)-2-aminocyclohexyl]amino}-4-{[1-(4-hydroxybenzyl)-1H-indol-4-yl]amino}pyrimidine-5-carboxamide;

2-{[(1R,2S)-2-aminocyclohexyl]amino}-4-[(1-benzyl-1H-indol-5-yl)amino]pyrimidine-5-carboxamide;

2-{[(1R,2S)-2-aminocyclohexyl]amino}-4-({1-[2-(4-hydroxyphenyl)ethyl]-1H-indol-4-yl}amino)pyrimidine-5-carboxamide;

2-{[(1R,2S)-2-aminocyclohexyl]amino}-4-({1-[3-(4-hydroxyphenyl)propyl]-1H-indol-4-yl}amino)pyrimidine-5-carboxamide;

2-{[(1R*,2S*)-2-aminocyclohexyl]amino}-4-{[1-(3-hydroxybenzyl)-1H-indol-4-yl]amino}pyrimidine-5-carboxamide;

2-{[(1R*,2S*)-2-aminocyclohexyl]amino}-4-{[1-(3-phenylpropyl)-1H-indol-4-yl]amino}pyrimidine-5-carboxamide;

2-{[(1R*,2S*)-2-aminocyclohexyl]amino}-4-({1-[2-(3-methoxyphenyl)ethyl]-1H-indol-4-yl}amino)pyrimidine-5-carboxamide;

2-{[(1R,2S)-2-aminocyclohexyl]amino}-4-({1-[2-(4-methoxyphenyl)ethyl]-1H-indol-4-yl}amino)pyrimidine-5-carboxamide;

methyl 7-[(2-{[(1R*,2S*)-2-aminocyclohexyl]amino}-5-carbamoylpyrimidin-4-yl)amino]-3,4-dihydroisoquinoline-2(1H)-carboxylate;

2-{[(1R*,2S*)-2-aminocyclohexyl]amino}-4-({1-[2-(2-methoxyphenyl)ethyl]-1H-indol-4-yl}amino)pyrimidine-5-carboxamide;

ethyl 7-[(2-{[(1R*,2S*)-2-aminocyclohexyl]amino}-5-carbamoylpyrimidin-4-yl)amino]-3,4-dihydroisoquinoline-2(1H)-carboxylate;

2-{[(1R*,2S*)-2-aminocyclohexyl]amino}-4-{[1-(2-phenylethyl)-1H-indol-4-yl]amino}pyrimidine-5-carboxamide;

2-{[(1R*,2S*)-2-aminocyclohexyl]amino}-4-{[2-(ethylsulfonyl)-1,2,3,4-tetrahydroisoquinolin-7-yl]amino}pyrimidine-5-carboxamide;

2-{[(1R,2S)-2-aminocyclohexyl]amino}-4-({1-[3-(4-methoxyphenyl)propyl]-1H-indol-4-yl}amino)pyrimidine-5-carboxamide;

2-{[(1R*,2S*)-2-aminocyclohexyl]amino}-4-[(1-benzyl-1H-indol-6-yl)amino]pyrimidine-5-carboxamide;

2-{[(1R*,2S*)-2-aminocyclohexyl]amino}-4-{[2-(2-hydroxybenzoyl)-1,2,3,4-tetrahydroisoquinolin-7-yl]amino}pyrimidine-5-carboxamide;

2-{[(1R*,2S*)-2-aminocyclohexyl]amino}-4-[(4'-chloro-3'-hydroxybiphenyl-3-yl)amino]pyrimidine-5-carboxamide;

phenyl 7-[(2-{[(1R*,2S*)-2-aminocyclohexyl]amino}-5-carbamoylpyrimidin-4-yl)amino]-3,4-dihydroisoquinoline-2(1H)-carboxylate;

2-{[(1R*,2S*)-2-aminocyclohexyl]amino}-4-{[2-(3-hydroxybenzoyl)-1,2,3,4-tetrahydroisoquinolin-7-yl]amino}pyrimidine-5-carboxamide;

2-{[(1R*,2S*)-2-aminocyclohexyl]amino}-4-[(2-benzoyl-1,2,3,4-tetrahydroisoquinolin-7-yl)amino]pyrimidine-5-carboxamide;

2-{[(1R*,2S*)-2-aminocyclohexyl]amino}-4-({2-[3-(methylthio)benzoyl]-1,2,3,4-tetrahydroisoquinolin-7-yl}amino)pyrimidine-5-carboxamide;

2-{[(1R*,2S*)-2-aminocyclohexyl]amino}-4-{[2-(benzylsulfonyl)-1,2,3,4-tetrahydroisoquinolin-7-yl]amino}pyrimidine-5-carboxamide;

isopropyl 7-[(2-{[(1R*,2S*)-2-aminocyclohexyl]amino}-5-carbamoylpyrimidin-4-yl)amino]-3,4-dihydroisoquinoline-2(1H)-carboxylate;

2-{[(1R*,2S*)-2-aminocyclohexyl]amino}-4-[(4'-chlorobiphenyl-3-yl)amino]pyrimidine-5-carboxamide;

2-{[(1R*,2S*)-2-aminocyclohexyl]amino}-4-({1-[3-(methylthio)benzyl]-1H-indol-4-yl}amino)pyrimidine-5-carboxamide;

4-[(2-acetyl-1,2,3,4-tetrahydroisoquinolin-7-yl)amino]-2-{[(1R*,2S*)-2-aminocyclohexyl]amino}pyrimidine-5-carboxamide;

2-{[(1R,2S)-2-aminocyclohexyl]amino}-4-{[1-(2-hydroxybenzyl)-1H-indol-4-yl]amino}pyrimidine-5-carboxamide;

benzyl 7-[(2-{[(1R*,2S*)-2-aminocyclohexyl]amino}-5-carbamoylpyrimidin-4-yl)amino]-3,4-dihydroisoquinoline-2(1H)-carboxylate;

2-{[(1R*,2S*)-2-aminocyclohexyl]amino}-4-{[2-(3-fluorobenzoyl)-1,2,3,4-tetrahydroisoquinolin-7-yl]amino}pyrimidine-5-carboxamide;

cyclopropyl 7-[(2-{[(1R*,2S*)-2-aminocyclohexyl]amino}-5-carbamoylpyrimidin-4-yl)amino]-3,4-dihydroisoquinoline-2(1H)-carboxylate;

2-{[(1R*,2S*)-2-aminocyclohexyl]amino}-4-{[2-(methylsulfonyl)-1,2,3,4-tetrahydroisoquinolin-7-yl]amino}pyrimidine-5-carboxamide;

2-{[(1R*,2S*)-2-aminocyclohexyl]amino}-4-{[1-(2-fluorobenzyl)-1H-indol-4-yl]amino}pyrimidine-5-carboxamide;

2-{[(1R*,2S*)-2-aminocyclohexyl]amino}-4-{[2-(cyclopropylsulfonyl)-1,2,3,4-tetrahydroisoquinolin-7-yl]amino}pyrimidine-5-carboxamide;

2-{[(1R*,2S*)-2-aminocyclohexyl]amino}-4-{[2-(4-fluorobenzoyl)-1,2,3,4-tetrahydroisoquinolin-7-yl]amino}pyrimidine-5-carboxamide;

2-{[(1R*,2S*)-2-aminocyclohexyl]amino}-4-({1-[4-(methylthio)benzyl]-1H-indol-4-yl}amino)pyrimidine-5-carboxamide;

2-{[(1R*,2S*)-2-aminocyclohexyl]amino}-4-[(2-pyridin-2-yl-1,2,3,4-tetrahydroisoquinolin-7-yl)amino]pyrimidine-5-carboxamide;

2-{[(1R*,2S*)-2-aminocyclohexyl]amino}-4-{[1-(2-methylbenzyl)-1H-indol-4-yl]amino}pyrimidine-5-carboxamide;

2-{[(1R*,2S*)-2-aminocyclohexyl]amino}-4-{[2-(3-methoxybenzoyl)-1,2,3,4-tetrahydroisoquinolin-7-yl]amino}pyrimidine-5-carboxamide;

2-{[(1R*,2S*)-2-aminocyclohexyl]amino}-4-{[2-(3-ethylbenzoyl)-1,2,3,4-tetrahydroisoquinolin-7-yl]amino}pyrimidine-5-carboxamide;

2-{[(1R*,2S*)-2-aminocyclohexyl]amino}-4-{[2-(cyclohexylcarbonyl)-1,2,3,4-tetrahydroisoquinolin-7-yl]amino}pyrimidine-5-carboxamide;

2-{[(1R*,2S*)-2-aminocyclohexyl]amino}-4-{[2-(isopropylsulfonyl)-1,2,3,4-tetrahydroisoquinolin-7-yl]amino}pyrimidine-5-carboxamide;
2-{[(1R*,2S*)-2-aminocyclohexyl]amino}-4-{[2-(2-methoxybenzoyl)-1,2,3,4-tetrahydroisoquinolin-7-yl]amino}pyrimidine-5-carboxamide;
2-{[(1R*,2S*)-2-aminocyclohexyl]amino}-4-{[2-(4-methylbenzoyl)-1,2,3,4-tetrahydroisoquinolin-7-yl]amino}pyrimidine-5-carboxamide;
2-{[(1R*,2S*)-2-aminocyclohexyl]amino}-4-{[2-(2-chlorobenzoyl)-1,2,3,4-tetrahydroisoquinolin-7-yl]amino}pyrimidine-5-carboxamide;
2-{[(1R*,2S*)-2-aminocyclohexyl]amino}-4-{[1-(2-chlorobenzyl)-1H-indol-4-yl]amino}pyrimidine-5-carboxamide;
2-{[(1R*,2S*)-2-aminocyclohexyl]amino}-4-{[2-(2-fluorobenzoyl)-1,2,3,4-tetrahydroisoquinolin-7-yl]amino}pyrimidine-5-carboxamide;
2-{[(1R*,2S*)-2-aminocyclohexyl]amino}-4-{[3-(phenoxymethyl)phenyl]amino}pyrimidine-5-carboxamide;
2-{[(1R*,2S*)-2-aminocyclohexyl]amino}-4-{[2-(4-chlorobenzoyl)-1,2,3,4-tetrahydroisoquinolin-7-yl]amino}pyrimidine-5-carboxamide;
2-{[(1R*,2S*)-2-aminocyclohexyl]amino}-4-{[2-(cyclopentylcarbonyl)-1,2,3,4-tetrahydroisoquinolin-7-yl]amino}pyrimidine-5-carboxamide;
2-{[(1R*,2S*)-2-aminocyclohexyl]amino}-4-{[1-(3-chlorobenzyl)-1H-indol-4-yl]amino}pyrimidine-5-carboxamide;
2-{[(1R*,2S*)-2-aminocyclohexyl]amino}-4-{[2-(3-methylbenzoyl)-1,2,3,4-tetrahydroisoquinolin-7-yl]amino}pyrimidine-5-carboxamide;
2-{[(1R*,2S*)-2-aminocyclohexyl]amino}-4-{[2-(cyclopropylcarbonyl)-1,2,3,4-tetrahydroisoquinolin-7-yl]amino}pyrimidine-5-carboxamide;
2-{[(1R*,2S*)-2-aminocyclohexyl]amino}-4-({2-[4-(methylthio)benzoyl]-1,2,3,4-tetrahydroisoquinolin-7-yl}amino)pyrimidine-5-carboxamide;
2-{[(1R*,2S*)-2-aminocyclohexyl]amino}-4-{[2-(4-ethylbenzoyl)-1,2,3,4-tetrahydroisoquinolin-7-yl]aminopyrimidine-5-carboxamide;
2-{[(1R*,2S*)-2-aminocyclohexyl]amino}-4-{[1-(3-methoxybenzyl)-1H-indol-6-yl]amino}pyrimidine-5-carboxamide;
2-{[(1R*,2S*)-2-aminocyclohexyl]amino}-4-{[1-(4-methoxybenzyl)-1H-indol-6-yl]amino}pyrimidine-5-carboxamide;
2-{[(1R*,2S*)-2-aminocyclohexyl]amino}-4-{[3-(4-methoxybenzyl)phenyl]amino}pyrimidine-5-carboxamide;
2-{[(1R*,2S*)-2-aminocyclohexyl]amino}-4-{[1-(2-methoxybenzyl)-1H-indol-6-yl]amino}pyrimidine-5-carboxamide;
2-{[(1R*,2S*)-2-aminocyclohexyl]amino}-4-{[2-(2-ethylbenzoyl)-1,2,3,4-tetrahydroisoquinolin-7-yl]amino}pyrimidine-5-carboxamide;
2-{[(1R*,2S*)-2-aminocyclohexyl]amino}-4-{[2-(3-chlorobenzoyl)-1,2,3,4-tetrahydroisoquinolin-7-yl]amino}pyrimidine-5-carboxamide;
2-{[(1R*,2S*)-2-aminocyclohexyl]amino}-4-{[2-(pyridin-2-ylcarbonyl)-1,2,3,4-tetrahydroisoquinolin-7-yl]amino}pyrimidine-5-carboxamide;
2-{[(1R*,2S*)-2-aminocyclohexyl]amino}-4-{[1-(3-phenoxybenzyl)-1H-indol-4-yl]amino}pyrimidine-5-carboxamide;
2-{[(1R*,2S*)-2-aminocyclohexyl]amino}-4-{[2-(4-methoxybenzoyl)-1,2,3,4-tetrahydroisoquinolin-7-yl]amino}pyrimidine-5-carboxamide;
2-{[(1R*,2S*)-2-aminocyclohexyl]amino}-4-({2-[2-(methylthio)benzoyl]-1,2,3,4-tetrahydroisoquinolin-7-yl}amino)pyrimidine-5-carboxamide;
2-{[(1R*,2S*)-2-aminocyclohexyl]amino}-4-{[3-(4-chlorobenzyl)phenyl]amino}pyrimidine-5-carboxamide;
2-{[(1R*,2S*)-2-aminocyclohexyl]amino}-{4-[1-(biphenyl-4-ylmethyl)-1H-indol-4-yl]amino}pyrimidine-5-carboxamide;
2-{[(1R*,2S*)-2-aminocyclohexyl]amino}-4-[(2-benzyl-1,2,3,4-tetrahydroisoquinolin-7-yl)amino]pyrimidine-5-carboxamide;
2-{[(1R*,2S*)-2-aminocyclohexyl]amino}-4-({3-[(3-hydroxyphenyl)thio]phenyl}amino)pyrimidine-5-carboxamide;
2-{[(1R*,2S*)-2-aminocyclohexyl]amino}-4-({3-[(4-hydroxyphenyl)thio]phenyl}amino)pyrimidine-5-carboxamide;
2-{[(1R*,2S*)-2-aminocyclohexyl]amino}-4-({3-[(4-methoxyphenyl)thio]phenyl}amino)pyrimidine-5-carboxamide;
2-{[(1R*,2S*)-2-aminocyclohexyl]amino}-4-{[2-(2-methylbenzoyl)-1,2,3,4-tetrahydroisoquinolin-7-yl]amino}pyrimidine-5-carboxamide;
2-{[(1R*,2S*)-2-aminocyclohexyl]amino}-4-{[1-(4-hydroxybenzyl)-1H-indol-6-yl]amino}pyrimidine-5-carboxamide;
2-{[(1R*,2S*)-2-aminocyclohexyl]amino}-4-{[3-(3-methylbenzyl)phenyl]amino}pyrimidine-5-carboxamide;
2-{[(1R,2S)-2-aminocyclohexyl]amino}-4-({3-[2-(methylamino)-2-oxoethoxy]phenyl}amino)pyrimidine-5-carboxamide;
2-{[(1R*,2S*)-2-aminocyclohexyl]amino}-4-{[1-(cyclopropylcarbonyl)-1,2,3,4-tetrahydroquinolin-7-yl]amino}pyrimidine-5-carboxamide;
2-{[(1R*,2S*)-2-aminocyclohexyl]amino}-4-({3-[(4-chlorophenyl)thio]phenyl}amino)pyrimidine-5-carboxamide;
2-{[(1R,2S)-2-aminocyclohexyl]amino}-{4-[1-(4-hydroxybenzyl)-1H-indol-4-yl]amino}pyrimidine-5-carboxamide;
2-{[(1R*,2S*)-2-aminocyclohexyl]amino}-4-{[2-(phenylsulfonyl)-1,2,3,4-tetrahydroisoquinolin-7-yl]amino}pyrimidine-5-carboxamide;
2-{[(1R*,2S*)-2-aminocyclohexyl]amino}-4-[(2-methyl-1,2,3,4-tetrahydroisoquinolin-7-yl)amino]pyrimidine-5-carboxamide;
2-{[(1R*,2S*R)-2-aminocyclohexyl]amino}-4-({3-[(3-methylphenyl)thio]phenyl}amino)pyrimidine-5-carboxamide;
2-{[(1R*,2S*)-2-aminocyclohexyl]amino}-4-{[1-(2-methoxybenzyl)-1H-indol-5-yl]amino}pyrimidine-5-carboxamide;
2-{[(1R*,2S*)-2-aminocyclohexyl]amino}-4-({3-[(3-methoxyphenyl)thio]phenyl}amino)pyrimidine-5-carboxamide;
2-{[(1R*,2S*)-2-aminocyclohexyl]amino}-4-[(3-benzylphenyl)amino]pyrimidine-5-carboxamide;
2-{[(1R,2S)-2-aminocyclohexyl]amino}-4-[(3'-hydroxybiphenyl-3-yl)amino]-6-methylpyrimidine-5-carboxamide;
2-{[(1R*,2S*)-2-aminocyclohexyl]amino}-4-{[3-(phenylthio)phenyl]amino}pyrimidine-5-carboxamide;

2-{[(1R*,2S*)-2-aminocyclohexyl]amino}-4-[(4-benzyl-phenyl)amino]pyrimidine-5-carboxamide;
2-{[(1R*,2S*)-2-aminocyclohexyl]amino}tetrahydroisoquinolin-7-ylamino)pyrimidine-5-carboxamide;
2-{[(1R*,2S*)-2-aminocyclohexyl]amino}-4-{[4-(phenylthio)phenyl]amino}pyrimidine-5-carboxamide;
2-{[(1R,2S)-2-aminocyclohexyl]amino}-4-[(4'-hydroxybiphenyl-3-yl)amino]-6-methylpyrimidine-5-carboxamide;
2-{[(1R*,2S*)-2-aminocyclohexyl]amino}-4-[(2-isobutyryl-1,2,3,4-tetrahydroisoquinolin-7-yl)amino]pyrimidine-5-carboxamide;
2-{[(1R*,2S*)-2-aminocyclohexyl]amino}-4-{[1-(cyclopropylcarbonyl)-1,2,3,4-tetrahydroquinolin-5-yl]amino}pyrimidine-5-carboxamide;
2-{[(1R*,2S*)-2-aminocyclohexyl]amino}-4-{[1-(2-phenoxybenzyl)-1H-indol-4-yl]amino}pyrimidine-5-carboxamide; and
a pharmaceutically acceptable salt thereof.

2. A pharmaceutical composition comprising a compound of claim 1, or a pharmaceutically acceptable salt thereof, and a pharmaceutically acceptable excipient.

3. A method for inhibiting spleen tyrosine kinase activity in a subject, comprising administering to the subject a therapeutically effective amount of a compound of claim 1, or a pharmaceutically acceptable salt thereof.

4. The method of claim 3, wherein the subject suffers from a disease or condition selected from the group consisting of chronic obstructive pulmonary disease, pulmonary vascular disease, cardiovascular disease, liver disease, inflammatory bowel disease, dry eye disease, autoimmune disease, Alzheimer's disease, allergic rhinitis, perennial rhinitis, nasal congestion, rhinorrhea, nasal inflammation, asthma, acute lung injury, acute bronchoconstriction, chronic bronchoconstriction, chronic eosinophilic pneumonia, chronic bronchitis, small airways obstruction, emphysema, adult respiratory distress syndrome, exacerbation of airways hyper-reactivity consequent to other drug therapy, bronchiectasis, sinusitis, allergic conjunctivitis, idiopathic pulmonary fibrosis, atopic dermatitis, inflammation, arthritis, pain, fever, pulmonary sarcoisosis, silicosis, cardiomyopathy, stroke, ischemia, reperfusion injury, brain edema, brain trauma, neurodegeneration, nephritis, retinitis, retinopathy, macular degeneration, glaucoma, diabetes, diabetic neuropathy, viral infection, bacterial infection, myalgia, endotoxic shock, toxic shock syndrome, osteoporosis, multiple sclerosis, endometriosis, menstrual cramps, vaginitis, candidiasis, cancer, conjunctivitis, food allergy, fibrosis, obesity, muscular dystrophy, polymyositis, skin flushing, eczema, psoriasis, rosacea, discoid lupus erythematosus, prurigo nodularis, alopecia and sunburn.

5. A compound:

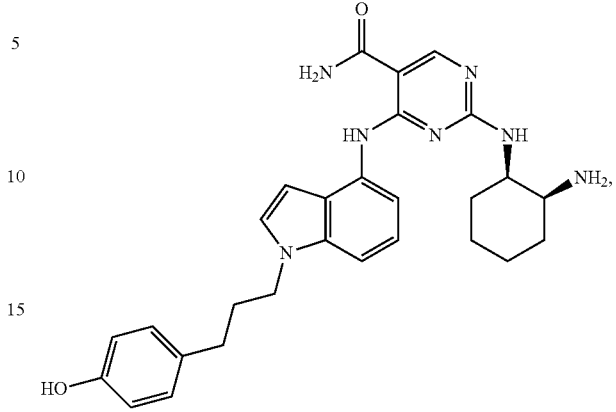

or a pharmaceutically acceptable salt thereof.

6. A pharmaceutical composition comprising a compound of claim 5, or a pharmaceutically acceptable salt thereof, and a pharmaceutically acceptable excipient.

7. A method for inhibiting spleen tyrosine kinase activity in a subject, comprising administering to the subject a therapeutically effective amount of a compound of claim 5, or a pharmaceutically acceptable salt thereof.

8. The method of claim 7, wherein the subject suffers from a disease or condition selected from the group consisting of chronic obstructive pulmonary disease, pulmonary vascular disease, cardiovascular disease, liver disease, inflammatory bowel disease, dry eye disease, autoimmune disease, Alzheimer's disease, allergic rhinitis, perennial rhinitis, nasal congestion, rhinorrhea, nasal inflammation, asthma, acute lung injury, acute bronchoconstriction, chronic bronchoconstriction, chronic eosinophilic pneumonia, chronic bronchitis, small airways obstruction, emphysema, adult respiratory distress syndrome, exacerbation of airways hyper-reactivity consequent to other drug therapy, bronchiectasis, sinusitis, allergic conjunctivitis, idiopathic pulmonary fibrosis, atopic dermatitis, inflammation, arthritis, pain, fever, pulmonary sarcoisosis, silicosis, cardiomyopathy, stroke, ischemia, reperfusion injury, brain edema, brain trauma, neurodegeneration, nephritis, retinitis, retinopathy, macular degeneration, glaucoma, diabetes, diabetic neuropathy, viral infection, bacterial infection, myalgia, endotoxic shock, toxic shock syndrome, osteoporosis, multiple sclerosis, endometriosis, menstrual cramps, vaginitis, candidiasis, cancer, conjunctivitis, food allergy, fibrosis, obesity, muscular dystrophy, polymyositis, skin flushing, eczema, psoriasis, rosacea, discoid lupus erythematosus, prurigo nodularis, alopecia and sunburn.

* * * * *

UNITED STATES PATENT AND TRADEMARK OFFICE
CERTIFICATE OF CORRECTION

PATENT NO. : 9,533,989 B2
APPLICATION NO. : 14/428808
DATED : January 3, 2017
INVENTOR(S) : Gavin A. Whitlock et al.

It is certified that error appears in the above-identified patent and that said Letters Patent is hereby corrected as shown below:

In the Claims

Column 40, Line 29, in Claim 1:

"2-{[(1R,2S*)-2-aminocyclohexyl]amino}-4-[(3'-hy-"

should read:

-- 2-{[(1R,2S)-2-aminocyclohexyl]amino}-4-[(3'-hy- --

Column 44, Line 10, in Claim 1:

"2-{[(1R*,2S*)-2-aminocyclohexyl]amino}-{4-[1-(biphe-"

should read:

-- 2-{[(1R*,2S*)-2-aminocyclohexyl]amino}-4-{[1-(biphe- --

Column 45, Line 4, in Claim 1:

"amino}tetrahydroisoquinolin-7-ylamino)pyrimidine-5-"

should read:

-- amino}-4-(1,2,3,4-tetrahydroisoquinolin-7-ylamino)pyrimidine-5- --

Signed and Sealed this
Fourteenth Day of March, 2017

Michelle K. Lee
*Director of the United States Patent and Trademark Office*